United States Patent
Larsen et al.

(10) Patent No.: US 10,918,796 B2
(45) Date of Patent: Feb. 16, 2021

(54) SYRINGE FOR MIXING TWO COMPONENTS AND FOR RETAINING A VACUUM IN A STORAGE CONDITION

(71) Applicant: Ferrosan Medical Devices A/S, Søborg (DK)

(72) Inventors: Kristian Larsen, Værløse (DK); Lise Sjørup Elle, Copenhagen K (DK); Thomas Ingemann Jensen, Copenhagen V (DK)

(73) Assignee: Ferrosan Medical Devices A/S, Søborg (DK)

( * ) Notice: Subject to any disclaimer, the term of this patent is extended or adjusted under 35 U.S.C. 154(b) by 259 days.

(21) Appl. No.: 15/580,181

(22) PCT Filed: Jun. 30, 2016

(86) PCT No.: PCT/EP2016/065260
§ 371 (c)(1),
(2) Date: Dec. 6, 2017

(87) PCT Pub. No.: WO2017/005590
PCT Pub. Date: Jan. 12, 2017

(65) Prior Publication Data
US 2018/0147355 A1 May 31, 2018

(30) Foreign Application Priority Data
Jul. 3, 2015 (EP) .................................. 15175189

(51) Int. Cl.
*A61M 5/20* (2006.01)
*A61M 5/24* (2006.01)
(Continued)

(52) U.S. Cl.
CPC ........ *A61M 5/2066* (2013.01); *A61M 5/2448* (2013.01); *A61M 5/2459* (2013.01);
(Continued)

(58) Field of Classification Search
CPC .............. A61M 5/2066; A61M 5/2448; A61M 5/2455; A61M 5/2466; A61M 5/2459;
(Continued)

(56) References Cited

U.S. PATENT DOCUMENTS

| | | | |
|---|---|---|---|
| 2,465,357 A | 3/1949 | Correll et al. | |
| 2,465,860 A | 3/1949 | Fleischmann | |

(Continued)

FOREIGN PATENT DOCUMENTS

| | | |
|---|---|---|
| BG | 0051589 | 7/1993 |
| BG | 0099900 | 3/1997 |

(Continued)

OTHER PUBLICATIONS

Notice of Allowability for U.S. Appl. No. 14/980,254, titled: "Dry Haemostatic Composition", dated Feb. 13, 2018.
(Continued)

*Primary Examiner* — Nilay J Shah
(74) *Attorney, Agent, or Firm* — Hamilton, Brook, Smith & Reynolds, P.C.

(57) ABSTRACT

A syringe for mixing two substances which have been retained separately inside the syringe is described, for instance in a storage condition. The syringe is used for 1) retaining a dry composition in a vacuum, and 2) mixing the dry composition with an aqueous medium to form a flowable substance. One embodiment, a syringe for retaining and mixing first and second substances comprises a barrel comprising a sealable and/or closable distal outlet and a vacuum chamber for holding a first substance, a plunger incorporating a reservoir chamber for holding a second substance and configured to be axially displaced through a proximal end of the barrel, a membrane separating the vacuum chamber and the reservoir chamber, and a pointed member, such as one or more needles, for penetrating the membrane, wherein the
(Continued)

syringe is configured such that the membrane and the pointed member are axially slidable in relation to each other.

25 Claims, 5 Drawing Sheets

(51) Int. Cl.
    *A61M 5/315*     (2006.01)
    *A61M 5/28*     (2006.01)
    *A61M 5/168*     (2006.01)
    *A61M 3/00*     (2006.01)

(52) U.S. Cl.
    CPC ......... *A61M 5/31596* (2013.01); *A61M 3/005* (2013.01); *A61M 5/16827* (2013.01); *A61M 5/2422* (2013.01); *A61M 5/2455* (2013.01); *A61M 5/2466* (2013.01); *A61M 5/284* (2013.01); *A61M 5/285* (2013.01); *A61M 5/286* (2013.01); *A61M 5/288* (2013.01); *A61M 5/31501* (2013.01); *A61M 2005/2086* (2013.01); *A61M 2005/247* (2013.01); *A61M 2005/2451* (2013.01); *A61M 2005/31598* (2013.01)

(58) Field of Classification Search
    CPC .. A61M 5/31596; A61M 5/285; A61M 5/286; A61M 5/288; A61M 5/16827; A61M 2005/247; A61M 2005/2451; A61M 3/005; A61M 5/31; A61M 5/31501; A61M 5/2422; A61M 1/1081; A61M 1/142
    See application file for complete search history.

(56) References Cited

U.S. PATENT DOCUMENTS

| | | |
|---|---|---|
| 2,507,244 A | 5/1950 | Correll |
| 2,558,395 A | 6/1951 | Studer |
| 2,899,362 A | 8/1959 | Sieger et al. |
| 3,089,815 A | 5/1963 | Kupelwieser et al. |
| 3,224,434 A | 12/1965 | Molomut et al. |
| 3,405,712 A * | 10/1968 | Pierick .................. A61M 5/284 604/88 |
| 3,514,518 A | 5/1970 | Charier-Vadrot |
| 3,608,593 A | 9/1971 | McCormick et al. |
| 3,678,933 A | 7/1972 | Moore et al. |
| 3,815,580 A | 6/1974 | Oster |
| 3,869,539 A | 3/1975 | Kring et al. |
| 3,892,876 A | 7/1975 | Hobday et al. |
| 3,899,606 A | 8/1975 | Forkner |
| 3,930,052 A | 12/1975 | De Brou et al. |
| 3,946,732 A | 3/1976 | Hurscham |
| 4,002,173 A | 1/1977 | Manning et al. |
| 4,006,220 A | 2/1977 | Gottlieb |
| 4,013,078 A | 3/1977 | Feild |
| 4,098,728 A | 7/1978 | Rosenblatt et al. |
| 4,107,288 A | 8/1978 | Oppenheim et al. |
| 4,124,705 A | 11/1978 | Rothman et al. |
| 4,150,744 A | 4/1979 | Fennimore |
| 4,160,022 A | 7/1979 | Delaney et al. |
| 4,164,559 A | 8/1979 | Miyata et al. |
| 4,179,400 A | 12/1979 | Tsao et al. |
| 4,194,392 A | 3/1980 | Lombard et al. |
| 4,208,439 A | 6/1980 | Hsu |
| 4,256,877 A | 3/1981 | Karlsson et al. |
| 4,265,233 A | 5/1981 | Sugitachi et al. |
| 4,280,954 A | 7/1981 | Yannas et al. |
| 4,291,013 A | 9/1981 | Wahlig et al. |
| 4,292,972 A | 10/1981 | Pawelchak et al. |
| 4,298,598 A | 11/1981 | Schwarz et al. |
| 4,300,494 A | 11/1981 | Graiff et al. |
| 4,320,201 A | 3/1982 | Berg et al. |
| 4,347,234 A | 8/1982 | Wahlig et al. |
| 4,362,567 A | 12/1982 | Schwarz et al. |
| 4,377,572 A | 3/1983 | Schwarz et al. |
| 4,416,813 A | 11/1983 | Ikeda et al. |
| 4,424,208 A | 1/1984 | Wallace et al. |
| 4,453,939 A | 6/1984 | Zimmerman |
| 4,482,386 A | 11/1984 | Wittwer et al. |
| 4,492,305 A | 1/1985 | Avery |
| 4,515,637 A | 5/1985 | Cioca |
| 4,522,302 A | 6/1985 | Paikoff |
| 4,536,387 A | 8/1985 | Sakamoto et al. |
| 4,540,410 A | 9/1985 | Wood et al. |
| 4,543,332 A | 9/1985 | Jao et al. |
| 4,549,554 A | 10/1985 | Markham |
| 4,554,156 A | 11/1985 | Fischer |
| 4,556,156 A | 12/1985 | Frutin |
| 4,557,377 A | 12/1985 | Maloney |
| 4,559,304 A | 12/1985 | Kasai et al. |
| 4,600,574 A | 7/1986 | Lindner et al. |
| 4,640,834 A | 2/1987 | Eibl et al. |
| 4,655,211 A | 4/1987 | Sakamoto et al. |
| 4,685,597 A | 8/1987 | Hirao et al. |
| 4,696,812 A | 9/1987 | Silbering |
| 4,702,737 A | 10/1987 | Pizzino |
| 4,735,616 A | 4/1988 | Eibl et al. |
| 4,743,229 A | 5/1988 | Chu |
| 4,746,514 A | 5/1988 | Warne |
| 4,749,689 A | 6/1988 | Miyata et al. |
| 4,752,466 A | 6/1988 | Saferstein et al. |
| 4,803,075 A | 2/1989 | Wallace et al. |
| 4,818,517 A | 4/1989 | Kwee et al. |
| 4,832,686 A | 5/1989 | Anderson |
| 4,837,285 A | 6/1989 | Berg et al. |
| 4,851,521 A | 7/1989 | Della Valle et al. |
| 4,861,714 A | 8/1989 | Dean, Jr. et al. |
| 4,863,856 A | 9/1989 | Dean, Jr. et al. |
| 4,885,161 A | 12/1989 | Cornell |
| 4,887,743 A | 12/1989 | Blake et al. |
| 4,891,359 A | 1/1990 | Saferstein et al. |
| 4,920,158 A | 4/1990 | Murray et al. |
| 4,925,677 A | 5/1990 | Feijen |
| 4,936,835 A | 6/1990 | Haaga et al. |
| 4,946,870 A | 8/1990 | Partain, III et al. |
| 4,948,575 A | 8/1990 | Cole et al. |
| 4,965,203 A | 10/1990 | Silbering et al. |
| 4,982,769 A | 1/1991 | Fournier et al. |
| 4,997,753 A | 3/1991 | Dean, Jr. et al. |
| 5,007,916 A | 4/1991 | Linsky et al. |
| 5,017,229 A | 5/1991 | Burns et al. |
| 5,023,082 A | 6/1991 | Friedman et al. |
| 5,024,841 A | 6/1991 | Chu et al. |
| 5,037,740 A | 8/1991 | Tanaka et al. |
| 5,041,292 A | 8/1991 | Feijen |
| 5,061,274 A | 10/1991 | Kensey |
| 5,061,492 A | 10/1991 | Okada et al. |
| 5,062,834 A | 11/1991 | Gross et al. |
| 5,080,893 A | 1/1992 | Goldberg et al. |
| 5,108,421 A | 4/1992 | Fowler |
| 5,112,750 A | 5/1992 | Tanaka et al. |
| 5,126,141 A | 6/1992 | Henry |
| 5,129,882 A | 7/1992 | Weldon et al. |
| 5,134,229 A | 7/1992 | Saferstein et al. |
| 5,135,751 A | 8/1992 | Henry et al. |
| 5,135,755 A | 8/1992 | Czech et al. |
| 5,140,016 A | 8/1992 | Goldberg et al. |
| 5,149,540 A | 9/1992 | Kunihiro et al. |
| 5,162,430 A | 11/1992 | Rhee et al. |
| 5,165,938 A | 11/1992 | Knighton |
| 5,178,883 A | 1/1993 | Knighton |
| 5,180,583 A | 1/1993 | Hedner |
| 5,192,300 A | 3/1993 | Fowler |
| 5,196,185 A | 3/1993 | Silver et al. |
| 5,204,382 A | 4/1993 | Wallace et al. |
| 5,209,776 A | 5/1993 | Bass et al. |
| 5,219,328 A | 6/1993 | Morse et al. |
| 5,275,616 A | 1/1994 | Fowler |
| 5,281,528 A | 1/1994 | Boctor et al. |
| 5,292,362 A | 3/1994 | Bass et al. |
| 5,300,494 A | 4/1994 | Brode, II et al. |

(56) References Cited

U.S. PATENT DOCUMENTS

| | | |
|---|---|---|
| 5,304,377 A | 4/1994 | Yamada et al. |
| 5,306,501 A | 4/1994 | Viegas et al. |
| 5,324,775 A | 6/1994 | Rhee et al. |
| 5,328,955 A | 7/1994 | Rhee et al. |
| 5,330,446 A | 7/1994 | Weldon et al. |
| 5,350,573 A | 9/1994 | Goldberg et al. |
| 5,350,581 A | 9/1994 | Kochinke |
| 5,352,715 A | 10/1994 | Wallace et al. |
| 5,356,614 A | 10/1994 | Sharma |
| 5,356,883 A | 10/1994 | Kuo et al. |
| 5,384,333 A | 1/1995 | Davis et al. |
| 5,385,606 A | 1/1995 | Kowanko |
| 5,387,208 A | 2/1995 | Ashton et al. |
| 5,394,886 A | 3/1995 | Nabai et al. |
| 5,397,704 A | 3/1995 | Boctor et al. |
| 5,399,361 A | 3/1995 | Song et al. |
| 5,401,511 A | 3/1995 | Margalit |
| 5,418,222 A | 5/1995 | Song et al. |
| 5,428,022 A | 6/1995 | Palefsky et al. |
| 5,428,024 A | 6/1995 | Chu et al. |
| 5,437,672 A | 8/1995 | Allyne |
| 5,441,491 A | 8/1995 | Verschoor et al. |
| 5,443,481 A | 8/1995 | Lee |
| 5,447,966 A | 9/1995 | Hermes et al. |
| 5,456,693 A | 10/1995 | Conston et al. |
| 5,462,860 A | 10/1995 | Mach |
| 5,478,352 A | 12/1995 | Fowler |
| 5,503,848 A | 4/1996 | Perbellini et al. |
| 5,507,744 A | 4/1996 | Tay et al. |
| 5,510,418 A | 4/1996 | Rhee et al. |
| 5,512,301 A | 4/1996 | Song et al. |
| 5,514,379 A | 5/1996 | Weissleder et al. |
| 5,516,532 A | 5/1996 | Atala et al. |
| 5,520,925 A | 5/1996 | Maser |
| 5,531,759 A | 7/1996 | Kensey et al. |
| 5,540,715 A | 7/1996 | Katsaros et al. |
| 5,580,923 A | 12/1996 | Yeung et al. |
| 5,595,735 A | 1/1997 | Saferstein et al. |
| 5,599,735 A | 2/1997 | Moslehi |
| 5,614,587 A | 3/1997 | Rhee et al. |
| 5,618,551 A | 4/1997 | Tardy et al. |
| 5,643,596 A | 7/1997 | Pruss et al. |
| 5,645,849 A | 7/1997 | Pruss et al. |
| 5,648,506 A | 7/1997 | Desai et al. |
| 5,658,592 A | 8/1997 | Tanihara et al. |
| 5,660,854 A | 8/1997 | Haynes et al. |
| 5,667,839 A | 9/1997 | Berg |
| 5,669,934 A | 9/1997 | Sawyer |
| 5,672,336 A | 9/1997 | Sharma |
| 5,674,275 A | 10/1997 | Tang et al. |
| 5,690,675 A | 11/1997 | Sawyer et al. |
| 5,690,954 A | 11/1997 | Ilium |
| 5,698,213 A | 12/1997 | Jamiolkowski et al. |
| 5,700,476 A | 12/1997 | Rosenthal et al. |
| 5,712,161 A | 1/1998 | Koezuka et al. |
| 5,714,370 A | 2/1998 | Eibl et al. |
| 5,723,308 A | 3/1998 | Mach et al. |
| 5,743,312 A | 4/1998 | Pfeifer et al. |
| 5,749,895 A | 5/1998 | Sawyer et al. |
| 5,752,974 A | 5/1998 | Rhee et al. |
| 5,770,229 A | 6/1998 | Tanihara et al. |
| 5,779,668 A | 7/1998 | Grabenkort |
| 5,791,352 A | 8/1998 | Reich et al. |
| 5,795,330 A | 8/1998 | Tofighi et al. |
| 5,798,091 A | 8/1998 | Trevino et al. |
| 5,804,203 A | 9/1998 | Hang et al. |
| 5,823,671 A | 10/1998 | Mitchell et al. |
| 5,824,015 A | 10/1998 | Sawyer |
| 5,853,749 A | 12/1998 | Hobbs |
| 5,856,356 A | 1/1999 | Tsouderos et al. |
| 5,861,043 A | 1/1999 | Carn |
| 5,863,496 A | 1/1999 | McElhany |
| 5,874,500 A | 2/1999 | Rhee et al. |
| 5,876,372 A | 3/1999 | Grabenkort et al. |
| 5,883,078 A | 3/1999 | Seelich et al. |
| 5,890,610 A | 4/1999 | Jansen et al. |
| 5,895,412 A | 4/1999 | Tucker |
| 5,902,832 A | 5/1999 | Van Bladel et al. |
| 5,908,054 A | 6/1999 | Safabash et al. |
| 5,931,165 A | 8/1999 | Reich et al. |
| 5,939,259 A | 8/1999 | Harvey et al. |
| 5,951,531 A | 9/1999 | Ferdman et al. |
| 5,951,583 A | 9/1999 | Jensen et al. |
| 5,957,166 A | 9/1999 | Safabash |
| 5,959,735 A | 9/1999 | Maris et al. |
| 5,986,168 A | 11/1999 | Noishiki et al. |
| 5,997,895 A | 12/1999 | Narotam et al. |
| 6,007,613 A | 12/1999 | Izoret |
| 6,027,741 A | 2/2000 | Cialdi et al. |
| 6,042,262 A | 3/2000 | Hajianpour |
| 6,045,570 A | 4/2000 | Epstein et al. |
| 6,056,970 A | 5/2000 | Greenawalt et al. |
| 6,063,061 A | 5/2000 | Wallace et al. |
| 6,066,325 A | 5/2000 | Wallace et al. |
| 6,074,663 A | 6/2000 | Delmottet et al. |
| 6,096,309 A | 8/2000 | Prior et al. |
| 6,099,952 A | 8/2000 | Cercone |
| 6,110,484 A | 8/2000 | Sierra |
| 6,113,948 A | 9/2000 | Heath |
| 6,129,761 A | 10/2000 | Hubbell |
| 6,132,759 A | 10/2000 | Schacht et al. |
| 6,146,587 A | 11/2000 | Morgan |
| 6,162,241 A | 12/2000 | Coury et al. |
| 6,166,130 A | 12/2000 | Rhee et al. |
| 6,168,788 B1 | 1/2001 | Wortham |
| 6,171,276 B1 * | 1/2001 | Lippe ............... A61M 5/20 128/DIG. 1 |
| 6,179,872 B1 | 1/2001 | Bell et al. |
| 6,193,670 B1 | 2/2001 | van Tassel et al. |
| 6,218,176 B1 | 4/2001 | Berthold et al. |
| 6,224,862 B1 | 5/2001 | Turecek et al. |
| 6,261,596 B1 | 7/2001 | Li et al. |
| 6,277,394 B1 | 8/2001 | Sierra |
| 6,280,727 B1 | 8/2001 | Prior et al. |
| 6,283,933 B1 | 9/2001 | D'Aiessio et al. |
| 6,300,128 B1 | 10/2001 | Morota et al. |
| 6,303,323 B1 | 10/2001 | Laskey et al. |
| 6,312,474 B1 | 11/2001 | Francis et al. |
| 6,312,725 B1 | 11/2001 | Wallace et al. |
| 6,321,951 B1 | 11/2001 | Frutin |
| 6,328,229 B1 | 12/2001 | Duronio et al. |
| 6,334,865 B1 | 1/2002 | Redmond et al. |
| 6,361,551 B1 | 3/2002 | Torgerson et al. |
| 6,364,519 B1 | 4/2002 | Hughes et al. |
| 6,387,413 B1 | 5/2002 | Miyata et al. |
| 6,391,343 B1 | 5/2002 | Yen |
| 6,416,739 B1 | 7/2002 | Rogerson |
| 6,423,037 B1 | 7/2002 | Hijikata et al. |
| 6,454,787 B1 | 9/2002 | Maddalo et al. |
| 6,458,380 B1 | 10/2002 | Leaderman |
| 6,458,386 B1 | 10/2002 | Schacht et al. |
| 6,458,889 B1 | 10/2002 | Trollsas |
| 6,461,325 B1 | 10/2002 | Delmotte et al. |
| 6,472,162 B1 | 10/2002 | Coelho |
| 6,495,127 B1 | 12/2002 | Wallace et al. |
| 6,548,081 B2 | 4/2003 | Sadozai et al. |
| 6,584,858 B1 | 7/2003 | Miyazawa et al. |
| 6,620,436 B1 | 9/2003 | Rolf |
| 6,635,272 B2 | 10/2003 | Leaderman |
| 6,638,538 B1 | 10/2003 | Hashimoto et al. |
| 6,649,162 B1 | 11/2003 | Biering et al. |
| 6,706,690 B2 | 3/2004 | Reich et al. |
| 6,716,435 B1 | 4/2004 | Farmer et al. |
| 6,733,774 B2 | 5/2004 | Stimmeder |
| 6,831,058 B1 | 12/2004 | Ikada et al. |
| 6,861,046 B1 | 3/2005 | Appino et al. |
| 6,887,974 B2 | 5/2005 | Pathak |
| 6,902,543 B1 * | 6/2005 | Cherif-Cheikh .... A61M 5/2448 604/82 |
| 7,052,713 B2 | 5/2006 | Stimmeder |
| 7,056,722 B1 | 6/2006 | Coelho |
| 7,109,163 B2 | 9/2006 | Pendharkar et al. |
| 7,125,860 B1 | 10/2006 | Renier et al. |
| 7,320,962 B2 | 1/2008 | Reich et al. |

(56) References Cited

U.S. PATENT DOCUMENTS

| | | |
|---|---|---|
| 7,393,674 B2 | 7/2008 | Jiang et al. |
| 7,427,607 B2 | 9/2008 | Suzuki |
| 7,435,425 B2 | 10/2008 | Qian et al. |
| 7,547,446 B2 | 6/2009 | Qian et al. |
| 7,833,965 B2 | 11/2010 | Pendharkar et al. |
| 7,871,637 B2 | 1/2011 | Qian et al. |
| 7,923,431 B2 | 4/2011 | Wolff |
| 7,927,626 B2 | 4/2011 | Pendharkar et al. |
| 7,935,371 B2 | 5/2011 | Williams |
| 8,071,090 B2 | 12/2011 | Senderoff et al. |
| 8,119,160 B2 | 2/2012 | Looney et al. |
| 8,303,981 B2 | 11/2012 | Wallace et al. |
| 8,329,119 B2 * | 12/2012 | Pearcy .................. B01L 3/0272 422/501 |
| 8,357,378 B2 | 1/2013 | Wallace et al. |
| 8,512,729 B2 | 8/2013 | Wallace et al. |
| 8,551,941 B2 | 10/2013 | Pendharkar et al. |
| 8,603,511 B2 | 12/2013 | Wallace et al. |
| 8,642,831 B2 | 2/2014 | Larsen et al. |
| 8,846,105 B2 | 9/2014 | Koopman et al. |
| 9,048,945 B2 | 6/2015 | Cordeiro |
| 9,265,858 B2 | 2/2016 | Larsen |
| 9,376,674 B2 | 6/2016 | Jorquera Nieto et al. |
| 9,446,848 B2 | 9/2016 | Jerome et al. |
| 9,533,069 B2 | 1/2017 | Larsen et al. |
| 9,629,798 B2 | 4/2017 | Senderoff et al. |
| 9,724,078 B2 | 8/2017 | Larsen et al. |
| 9,999,703 B2 | 6/2018 | Larsen |
| 10,111,980 B2 | 10/2018 | Larsen |
| 10,595,837 B2 | 3/2020 | Larsen et al. |
| 2001/0008636 A1 | 7/2001 | Yamamoto et al. |
| 2001/0038848 A1 | 11/2001 | Donda |
| 2001/0041913 A1 | 11/2001 | Cragg et al. |
| 2002/0006429 A1 | 1/2002 | Redmond et al. |
| 2002/0010150 A1 | 1/2002 | Cortese et al. |
| 2002/0010482 A1 | 1/2002 | Watt et al. |
| 2002/0012982 A1 | 1/2002 | Blakesley et al. |
| 2002/0015724 A1 | 2/2002 | Yang et al. |
| 2002/0019062 A1 | 2/2002 | Lea et al. |
| 2002/0025921 A1 | 2/2002 | Petito et al. |
| 2002/0026215 A1 | 2/2002 | Redmond et al. |
| 2002/0027146 A1 | 3/2002 | de LaForcade et al. |
| 2002/0039594 A1 | 4/2002 | Unger |
| 2002/0042378 A1 | 4/2002 | Reich et al. |
| 2002/0061842 A1 | 5/2002 | Mansour et al. |
| 2002/0072767 A1 | 6/2002 | Zhu |
| 2002/0082620 A1 | 6/2002 | Lee et al. |
| 2002/0111576 A1 | 8/2002 | Greene et al. |
| 2002/0164322 A1 | 11/2002 | Schaufler |
| 2002/0173818 A1 | 11/2002 | Reever |
| 2002/0188196 A1 | 12/2002 | Burbank et al. |
| 2002/0192271 A1 | 12/2002 | Hedner et al. |
| 2002/0193448 A1 | 12/2002 | Wallace et al. |
| 2003/0004449 A1 | 1/2003 | Lafratta et al. |
| 2003/0008831 A1 | 1/2003 | Yang et al. |
| 2003/0009194 A1 | 1/2003 | Saker et al. |
| 2003/0012741 A1 | 1/2003 | Furlan et al. |
| 2003/0028140 A1 | 2/2003 | Greff |
| 2003/0032143 A1 | 2/2003 | Neff et al. |
| 2003/0040701 A1 | 2/2003 | Dalmose |
| 2003/0064109 A1 | 4/2003 | Qian et al. |
| 2003/0095993 A1 | 5/2003 | Benz et al. |
| 2003/0162708 A1 | 8/2003 | Wolff |
| 2003/0175410 A1 | 9/2003 | Campbell |
| 2003/0175419 A1 | 9/2003 | Sessa |
| 2003/0181659 A1 | 9/2003 | Naranda et al. |
| 2003/0224056 A1 | 12/2003 | Kotha et al. |
| 2003/0225378 A1 | 12/2003 | Wilkie et al. |
| 2003/0232746 A1 | 12/2003 | Lamberti et al. |
| 2004/0062790 A1 | 4/2004 | Constantine et al. |
| 2004/0076647 A1 | 4/2004 | Biering |
| 2004/0079763 A1 | 4/2004 | Powell et al. |
| 2004/0101546 A1 | 5/2004 | Gorman et al. |
| 2004/0120993 A1 | 6/2004 | Zhang et al. |
| 2004/0186432 A1 | 9/2004 | Barry et al. |
| 2004/0197388 A1 | 10/2004 | Sceusa |
| 2004/0214770 A1 | 10/2004 | Reich et al. |
| 2004/0243043 A1 | 12/2004 | McCarthy et al. |
| 2004/0267352 A1 | 12/2004 | Davidson et al. |
| 2005/0008632 A1 | 1/2005 | Stimmeder |
| 2005/0031691 A1 | 2/2005 | McGurk et al. |
| 2005/0137512 A1 | 6/2005 | Campbell et al. |
| 2005/0171001 A1 | 8/2005 | Pendharkar et al. |
| 2005/0186253 A1 | 8/2005 | Lee et al. |
| 2005/0214277 A1 | 9/2005 | Schaufler |
| 2005/0218541 A1 | 10/2005 | Peng et al. |
| 2005/0239675 A1 | 10/2005 | Makansi |
| 2005/0245905 A1 | 11/2005 | Schmidt et al. |
| 2005/0284809 A1 | 12/2005 | Looney et al. |
| 2006/0002890 A1 | 1/2006 | Hersel et al. |
| 2006/0002918 A1 | 1/2006 | Jiang et al. |
| 2006/0052747 A1 * | 3/2006 | Nishimura ............ A61M 5/288 604/85 |
| 2006/0067976 A1 | 3/2006 | Ferraro et al. |
| 2006/0068013 A1 | 3/2006 | DiTizio et al. |
| 2006/0115805 A1 | 6/2006 | Hansen |
| 2006/0121080 A1 | 6/2006 | Lye et al. |
| 2006/0121104 A1 | 6/2006 | Stern |
| 2006/0147492 A1 | 7/2006 | Hunter et al. |
| 2006/0159733 A1 | 7/2006 | Pendharkar et al. |
| 2006/0167561 A1 | 7/2006 | Odar et al. |
| 2006/0189516 A1 | 8/2006 | Yang et al. |
| 2006/0193846 A1 | 8/2006 | Stimmeder |
| 2006/0204490 A1 | 9/2006 | Pendharkar et al. |
| 2006/0255053 A1 | 11/2006 | Li |
| 2006/0282138 A1 | 12/2006 | Ota |
| 2007/0009578 A1 | 1/2007 | Moiler et al. |
| 2007/0025955 A1 | 2/2007 | Lowinger et al. |
| 2007/0054020 A1 | 3/2007 | Kumagai |
| 2007/0086958 A1 | 4/2007 | Drake et al. |
| 2007/0128343 A1 | 6/2007 | Chappa |
| 2007/0160543 A1 | 7/2007 | Moiler |
| 2007/0215235 A1 | 9/2007 | Ranalletta et al. |
| 2007/0217282 A1 * | 9/2007 | Lidgren ............. A61B 17/8816 366/108 |
| 2007/0250007 A1 | 10/2007 | Shekalim |
| 2007/0264130 A1 | 11/2007 | Mallett |
| 2007/0264301 A1 | 11/2007 | Cleek et al. |
| 2007/0264302 A1 | 11/2007 | Cleek et al. |
| 2008/0029087 A1 | 2/2008 | Kidd, III |
| 2008/0085316 A1 | 4/2008 | Qian et al. |
| 2008/0091277 A1 | 4/2008 | Deusch et al. |
| 2008/0095830 A1 | 4/2008 | Van Holten |
| 2008/0109002 A1 | 5/2008 | Delmotte |
| 2008/0199539 A1 | 8/2008 | Baker et al. |
| 2008/0286376 A1 | 11/2008 | Qian et al. |
| 2008/0311172 A1 | 12/2008 | Schapira et al. |
| 2009/0087569 A1 | 4/2009 | Fan et al. |
| 2009/0142396 A1 | 6/2009 | Odar et al. |
| 2009/0157017 A1 | 6/2009 | Ambrosio |
| 2010/0028309 A1 | 2/2010 | Odar et al. |
| 2010/0048758 A1 | 2/2010 | Chen et al. |
| 2010/0063459 A1 | 3/2010 | Preiss-Bloom et al. |
| 2010/0113828 A1 | 5/2010 | Dalsin et al. |
| 2010/0143447 A1 | 6/2010 | Hansen |
| 2010/0256671 A1 | 10/2010 | Falus |
| 2010/0292717 A1 | 11/2010 | Petter-Puchner et al. |
| 2010/0318048 A1 | 12/2010 | Hoeffinghoff et al. |
| 2011/0021964 A1 | 1/2011 | Larsen et al. |
| 2011/0045034 A1 | 2/2011 | Nur et al. |
| 2011/0059228 A1 | 3/2011 | Gillick et al. |
| 2011/0270167 A1 | 11/2011 | Matusch |
| 2012/0128653 A1 | 5/2012 | Goessl et al. |
| 2012/0201726 A1 | 8/2012 | Pearcy et al. |
| 2014/0220130 A1 | 8/2014 | Larsen et al. |
| 2015/0037314 A1 | 2/2015 | Larsen |
| 2015/0045830 A1 | 2/2015 | Jensen et al. |
| 2016/0120527 A1 | 5/2016 | Larsen et al. |
| 2016/0354512 A1 | 12/2016 | Larsen |
| 2018/0243468 A1 | 8/2018 | Larsen |

(56) References Cited

U.S. PATENT DOCUMENTS

| | | | |
|---|---|---|---|
| 2018/0264194 A1 | 9/2018 | Larsen | |
| 2019/0015546 A1 | 1/2019 | Larsen | |

FOREIGN PATENT DOCUMENTS

| | | |
|---|---|---|
| CN | 1270240 | 10/2000 |
| DE | 2316209 A1 | 10/1974 |
| DE | 3146841 | 6/1983 |
| DE | 4119140 | 12/1992 |
| DE | 4407875 | 9/1995 |
| EP | 0132983 | 2/1985 |
| EP | 0156649 | 10/1985 |
| EP | 0282316 | 9/1988 |
| EP | 0341007 | 11/1989 |
| EP | 0341745 | 11/1989 |
| EP | 0365705 | 5/1990 |
| EP | 0372966 | 6/1990 |
| EP | 0385916 A2 | 9/1990 |
| EP | 0395758 | 11/1990 |
| EP | 0172710 | 3/1992 |
| EP | 0478827 | 4/1992 |
| EP | 0493387 | 10/1993 |
| EP | 0376931 | 6/1994 |
| EP | 0702081 | 3/1996 |
| EP | 0737467 | 10/1996 |
| EP | 0612252 | 5/1999 |
| EP | 0773740 | 11/1999 |
| EP | 1005874 | 6/2000 |
| EP | 1022031 | 7/2000 |
| EP | 1044693 | 10/2000 |
| EP | 1053758 | 11/2000 |
| EP | 1084720 | 3/2001 |
| EP | 1140235 | 10/2001 |
| EP | 1174463 | 1/2002 |
| EP | 1258256 | 11/2002 |
| EP | 1283063 | 2/2003 |
| EP | 0790823 | 7/2003 |
| EP | 0891193 | 8/2003 |
| EP | 1484070 | 12/2004 |
| EP | 1 543 842 A1 | 6/2005 |
| EP | 1095064 | 6/2005 |
| EP | 1649867 | 4/2006 |
| EP | 1361906 | 4/2007 |
| EP | 1414370 | 4/2007 |
| EP | 1059957 | 8/2007 |
| EP | 1608230 | 7/2010 |
| EP | 2 040 724 B1 | 10/2011 |
| FR | 2679772 | 5/1993 |
| FR | 2759980 | 8/1998 |
| GB | 648619 | 1/1951 |
| GB | 697603 | 9/1953 |
| GB | 1037937 | 8/1966 |
| GB | 1199887 | 7/1970 |
| GB | 1 483 002 | 7/1975 |
| GB | 1584080 | 2/1981 |
| GB | 1591654 | 6/1981 |
| GB | 2266239 | 10/1993 |
| GB | 2393120 | 3/2004 |
| GB | 2414021 | 11/2005 |
| JP | 51-125156 | 11/1976 |
| JP | 59-113889 | 6/1984 |
| JP | 60214728 | 10/1985 |
| JP | 62070318 | 3/1987 |
| JP | 62221357 | 9/1987 |
| JP | 01130519 | 5/1989 |
| JP | 05308969 | 11/1993 |
| JP | 06254148 | 9/1994 |
| JP | H07090241 | 4/1995 |
| JP | 08-024325 | 1/1996 |
| JP | 9-504719 | 5/1997 |
| JP | 10-507666 | 7/1998 |
| JP | 2002/513308 | 5/2002 |
| JP | 2004002271 | 1/2004 |
| JP | 2004147959 | 5/2004 |
| JP | 2006-296896 | 11/2006 |
| JP | 2010228932 | 10/2010 |
| JP | 2011212182 A | 10/2011 |
| KR | 910007847 | 10/1991 |
| KR | 100751046 | 8/2007 |
| WO | WO 83/01244 | 4/1983 |
| WO | WO 86/00912 | 2/1986 |
| WO | WO 89/02730 | 4/1989 |
| WO | WO 90/13320 | 11/1990 |
| WO | WO 92/21354 | 12/1992 |
| WO | WO 92/22252 | 12/1992 |
| WO | WO 93/06802 | 4/1993 |
| WO | WO 93/06855 | 4/1993 |
| WO | WO 93/10768 | 6/1993 |
| WO | WO 93/21908 | 11/1993 |
| WO | WO 94/08552 | 4/1994 |
| WO | WO 94/17840 | 8/1994 |
| WO | WO 94/27630 | 12/1994 |
| WO | WO 95/12371 | 5/1995 |
| WO | WO 95/15747 | 6/1995 |
| WO | WO 95/25748 | 9/1995 |
| WO | WO 95/31955 | 11/1995 |
| WO | WO 96/04025 | 2/1996 |
| WO | WO 96/06883 | 3/1996 |
| WO | WO 96/07472 | 3/1996 |
| WO | WO 96/10374 | 4/1996 |
| WO | WO 96/10428 | 4/1996 |
| WO | WO 96/12447 | 5/1996 |
| WO | WO 96/14368 | 5/1996 |
| WO | WO 96/16643 | 6/1996 |
| WO | WO 96/39159 | 12/1996 |
| WO | WO 96/40033 | 12/1996 |
| WO | WO 97/17023 | 5/1997 |
| WO | WO 97/17024 | 5/1997 |
| WO | WO 97/17025 | 5/1997 |
| WO | WO 97/29792 | 8/1997 |
| WO | WO 97/37694 | 10/1997 |
| WO | WO 98/08550 | 3/1998 |
| WO | WO 98/31403 | 7/1998 |
| WO | WO 98/34546 | 8/1998 |
| WO | WO 98/36784 | 8/1998 |
| WO | WO 98/43092 | 10/1998 |
| WO | WO 98/44963 | 10/1998 |
| WO | WO 98/51282 | 11/1998 |
| WO | WO 99/04828 | 2/1999 |
| WO | WO 99/12032 | 3/1999 |
| WO | WO 99/13902 | 3/1999 |
| WO | WO 99/38606 | 8/1999 |
| WO | WO 99/44901 | 9/1999 |
| WO | WO 99/45938 | 9/1999 |
| WO | WO 99/051208 | 10/1999 |
| WO | WO 00/09018 | 2/2000 |
| WO | WO 00/18301 | 4/2000 |
| WO | WO 00/27327 | 5/2000 |
| WO | WO 00/61201 | 10/2000 |
| WO | WO 00/74742 | 12/2000 |
| WO | WO 00/76533 | 12/2000 |
| WO | WO 01/13956 | 3/2001 |
| WO | WO 01/28603 | 4/2001 |
| WO | WO 01/34206 | 5/2001 |
| WO | WO 01/54735 | 8/2001 |
| WO | WO 01/66161 | 9/2001 |
| WO | WO 01/97826 | 12/2001 |
| WO | WO 01/97871 A2 | 12/2001 |
| WO | WO 02/18450 | 3/2002 |
| WO | WO 02/22059 | 3/2002 |
| WO | WO 02/22184 | 3/2002 |
| WO | WO 02/40068 | 5/2002 |
| WO | WO 02/058749 | 8/2002 |
| WO | WO 02/064182 | 8/2002 |
| WO | WO 02/070594 | 9/2002 |
| WO | WO 02/072128 A1 | 9/2002 |
| WO | 202096488 | 12/2002 |
| WO | WO 03/007845 | 1/2003 |
| WO | WO 2003/004072 | 1/2003 |
| WO | WO 03/024426 | 3/2003 |
| WO | WO 03/024429 | 3/2003 |
| WO | WO 03/055531 | 7/2003 |
| WO | WO 2003/070110 | 8/2003 |
| WO | WO 03/074103 A2 | 9/2003 |

(56) References Cited

FOREIGN PATENT DOCUMENTS

| | | |
|---|---|---|
| WO | WO 03/094983 | 11/2003 |
| WO | WO 04/028404 | 4/2004 |
| WO | WO 04/028423 | 4/2004 |
| WO | WO 04/029095 | 4/2004 |
| WO | WO 04/030711 | 4/2004 |
| WO | WO 2004/026377 A1 | 4/2004 |
| WO | WO 2004/028583 | 4/2004 |
| WO | WO 2004/035629 | 4/2004 |
| WO | WO 2004/053051 | 6/2004 |
| WO | WO 2004/069303 A2 | 8/2004 |
| WO | WO 04/075650 | 9/2004 |
| WO | WO 04/084869 | 10/2004 |
| WO | WO 04/108035 | 12/2004 |
| WO | WO 2004/108179 | 12/2004 |
| WO | WO 2004/108418 A1 | 12/2004 |
| WO | WO 05/000265 | 1/2005 |
| WO | WO 2005/002510 A2 | 1/2005 |
| WO | WO 05/009225 | 2/2005 |
| WO | WO 05/041811 | 5/2005 |
| WO | WO 05/044285 | 5/2005 |
| WO | WO 05/062889 | 7/2005 |
| WO | WO 05/063217 A1 | 7/2005 |
| WO | WO 2005/072700 | 8/2005 |
| WO | WO 2005/084650 A1 | 9/2005 |
| WO | WO 05/107713 | 11/2005 |
| WO | WO 2006/005340 | 1/2006 |
| WO | WO 2006/031358 | 3/2006 |
| WO | WO 06/034568 | 4/2006 |
| WO | WO 06/063758 | 6/2006 |
| WO | WO 2006/058435 A2 | 6/2006 |
| WO | WO 06/128471 | 12/2006 |
| WO | WO 2007/001926 | 1/2007 |
| WO | WO 2007/018887 A2 | 2/2007 |
| WO | WO 2007/092618 A2 | 8/2007 |
| WO | WO 2007/133699 | 11/2007 |
| WO | WO 2007/137839 | 12/2007 |
| WO | 2008019127 A2 | 2/2008 |
| WO | WO 2008/016983 | 2/2008 |
| WO | 2008060475 A2 | 5/2008 |
| WO | WO 2008/051758 | 5/2008 |
| WO | WO 2008/090555 | 7/2008 |
| WO | WO 2009/020612 | 2/2009 |
| WO | WO 2009/109194 | 9/2009 |
| WO | WO 2009/109963 | 9/2009 |
| WO | WO 2009/131752 A2 | 10/2009 |
| WO | WO 2011/047753 A1 | 4/2011 |
| WO | WO 2011/137437 A2 | 11/2011 |
| WO | WO 2011/151384 | 12/2011 |
| WO | WO 2011/151386 | 12/2011 |
| WO | WO 2011/151400 | 12/2011 |
| WO | WO 2012/146655 | 11/2012 |
| WO | WO 2013/053753 | 4/2013 |
| WO | WO 2013/053755 | 4/2013 |
| WO | WO 2013/053759 | 4/2013 |
| WO | WO 2013/060770 | 5/2013 |
| WO | WO 2013/112579 A1 | 8/2013 |
| WO | WO 2013/131520 A2 | 9/2013 |
| WO | WO 2013/185776 A1 | 12/2013 |
| WO | WO 2014/086996 | 6/2014 |
| WO | WO 2014/0202760 A2 | 12/2014 |
| WO | WO 2015/086028 A1 | 6/2015 |
| WO | WO 2016/058612 A1 | 4/2016 |
| WO | WO 2017/098493 A1 | 6/2017 |

OTHER PUBLICATIONS

Office Action for U.S. Appl. No. 15/102,994, titled: "Dry Composition Comprising an Extrusion Enhancer", dated Feb. 22, 2018.
Notice of Allowance for U.S. Appl. No. 15/102,994, titled: "Dry Composition Comprising an Extrusion Enhancer", dated Jun. 22, 2018.
Office Action for U.S. Appl. No. 15/639,237, titled: "Vacuum Expanded Dry Composition and Syringe for Retaining Same", dated Aug. 8, 2018.
Final Office Action for U.S. Appl. No. 15/639,237, titled: "Vacuum Expanded Dry Composition and Syringe for Retaining Same", dated Nov. 30, 2018.
Final Office Action for U.S. Appl. No. 14/383,461, titled: "Pressurized Container Containing Haemostatic Paste", dated Jan. 8, 2019.
Office Action for U.S. Appl. No. 15/639,237, titled: "Vacuum Expanded Dry Composition and Syringe for Retaining Same", dated May 8, 2019.
"Formulation and Evaluation of Absorbable Gelatin Sponges," Chapter 3A of Rupali Kale thesis: Design and Development of Surgical Dressings for Advanced Wound Management (2010).
"Gelfoam Prescribing Information," Pharmacia & Upjohn (Nov. 1996).
"Gelfoam® Product Brochure," Pharmacia & Upjohn (Jun. 2013).
26th Annual Symposium: Clinical Update in Anaesthesiology, Surgery and Perioperative Medicine, Jan. 20-25, 2008.
Ansell, J., et al., "Gelfoam and Autologous Clot Embolization: Effect on Coagulation," Investigative Radiology, 13: 115-120 (1978).
Arai, K., et al., "Clinical Effect of Thrombin-Collagen Sponge Sheet in Surgical Field," Chiryo (Pharmacology and Treatment), 11(5):413-418 (1983). (English translation of Office Action for Japanese counterpart application 2010-547957, Title: Device for Promotion of Hemostasis and/or Wound Healing, being provided to satisfy "concise explanation" requirement under 37 C.F.R. 1.98(a)(3)).
Barrow, D.L., et al., "The Use of Greater Omentum Vascularized Free Flaps for Neurosurgical Disorders Requiring Reconstruction", Journal of Neurosurgery, 60: 305-311 (1984).
Barton, B., et al., "Fibrin Glue as a Biologic Vascular Patch—A Comparative Study," Journal of Surgical Research, vol. 40, 1 page; abstract retrieved from http://www.ncbi.nlm.nih.gov on Jan. 3, 2001. (1986).
Baxter, "Product Catalogue: Collagen," 4 pages, retrieved from http://www.baxter-ecommerce.com/ecatalog on Feb. 2, 2006 (2006).
Baxter, "TissuFleece E Package Leaflet," Baxter International Inc., 4 pages, English portion of instructions for use (2003).
Baxter, "TissuFleece E, TissuCone E and TissuFoil E: Biomaterials," Basic scientific Information, 9 pages (2003).
Boland, T., et al., "Application of Inkjet Printing to Tissue Engineering," Biotechnol. J., 1: 910-917 (2006).
Boyers, S., et al., "Reduction of Postoperative Pelvic Adhesions in the Rabbit with Gore-Tex Surgical Membrane", Fertility and Sterility, 49(6,): 1066-1070 (1988).
Brannon-Peppas, L., et al., "The Equilibrium Swelling Behavior of Porous and Non-Porous Hydrogels," Absorbent Polymer Technology, Elsevier, Amsterdam, pp. 67-102 (1990).
Branski, R.C., et al., "Mucosal Wound Healing in a Rabbit Model of Subglottic Stenosis"; Arch Otolaryngol Head Neck Surg, vol. 131, Feb. 2005, p. 153-157.
Brunt and Klausner, "Growth factors speed wound healing", Nature Biotechnology, 6(1): 25-30 (1988).
Campbell, P.G., et al., "Engineered Spatial Patterns of FGF-2 Immobilized on Fibrin Direct Cell Organization," Biomaterials, 26: 6762-6770 (2005).
Campbell, P.G., et al., "Tissue Engineering with the Aid of Inkjet Printers," Expert Opin. Biol. Ther., 7: 1123-1127 (2007).
Canal, T., et al., "Correlation Between Mesh Size and Equilibrium Degree of Swelling of Polymeric Networks" Biomedical Materials Research, 23: 1183-1193 (1989).
Cantor, M.O., et al., "Gelfoam® and Thrombin in treatment of massive gastroduodenal hemorrhage—A preliminary report", American Journal of Surgery, 883-887 (Dec. 1950).
Cantor, M.O., et al., "Gelfoam and Thrombin in Gastroduodenal Bleeding: An Experimental Study," Journal of Laboratory and Clinical Medicine, 35(6): 890-893 (1950).
Cantor, M.O., et al., "Gelfoam and Thrombin in Treatment of Massive Upper Gastrointestinal Hemorrhage," American Journal of Surgery, 82(2): 230-235 (Aug. 1951).
Cascone, M.G., et al., "Collagen and hyaluronic acid based polymeric blends as drug delivery systems for the release of physiological concentrations of growth hormone." Journal of Materials science: Materials in Medicine; 5: 770-774 (1994).
Changez, M., et al., Abstract of "Efficacy of antibiotics-loaded interpenetrating network (IPNs) hydrogel based on poly (acrylic

(56) References Cited

OTHER PUBLICATIONS acid) and gelatin for treatment of experimental osteomyelitis: in vivo study.", Biomaterials; 26(14): 2095-2104 (2005).
Chaplin, J.M., et al., "Use of an Acellular Dermal Allograft for Dural Replacement: An Experimental Study," Neurosurgery, 45(2): 320-327 (1999).
Cheung, D., et al., "Mechanism of Crosslinking of Proteins by Glutaraldehyde IV: In Vitro and In Vivo Stability of a Crosslinked Collagen Matrix," Connective Tissue Research, 25: 27-34 (1990).
Choi, Y.S., et al., "Studies on Gelatin-Based Sponges. Part Ill: A Comparative Study of Cross-linked Gelatin/ Alginate, Gelatin/ Hyaluronate and Chitosan/Hyaluronate Sponges and their Application as a wound dressing in fullthickness skin defect of rat.", J. of Mat. Sci.; Mat. in Med.; 12: 67-73 (Jan. 2001).
Choi, Y.S., et al., "Studies on gelatin-containing artificial skin: II. Preparation and characterization of cross-linked gelatin-hyaluronate sponge.", J. Biomed Mater Res., 48: 631-639 (1999).
Christensen, F, et al., "Qualitative Description of the Wurster-Based Fluid-Bed Coating Process," Drug Dev and Industry Pharmacy, 23(5): 451-463 (1977).
Chronic Wound Care Guidelines © 2007 http://woundheal.org.documents/final_pocket_guide_treatment.aspx.
Chuang, V.P., et al., "Sheath Needle for Liver Biopsy in High-Risk Patients" Radiology, 166: 261-262 (1988).
Coenye, K.E., et al., "A Qualitative Morphological comparison of Two Heamostatic Agents in a Porcine Liver Trauma Model," Surgical Science, 4: 359-364 (2013).
Collins, D., et al., "Enemata of Gelfoam Milk Suspension Combined with Thrombin-Solution to Control Massive Hemorrhage Following Anorectal Surgery," The American Journal of Proctology, 2: 60-63 (1951).
Collins, R., et al., "Use of Collagen Film as a Dural Substitute: Preliminary Animal Studies," Journal of Biomedical Materials Research, 25: 267-276 (1991).
De la Torre, R.A., et al., "Hemostasis and Hemostatic agents in minimally invasive surgery", Surgery, 142(4S): S39-S45 (2007).
De laco, P.A., et al., "Efficacy of a Hyaluronan Derivative gel in postsurgical adhesion prevention in the presence of inadequate hemostasis." Surgery, 130(1): 60-64 (2001).
DeLustro, F., et al., "A Comparative Study of the Biologic and Immunologic Response to Medical Devices Derived From Dermal Collagen," Journal of Biomedical Materials Research, 20: 109-120 (1986).
Dembo, M.A., et al., Abstract of "Antiseptic hemostatic preparations, their properties and study", Lech. Prep. Krovi Tkanei; pp. 139-140 (1974).
Dodd, G.D., et al., "Minimally invasive treatment of malignant hepatic tumors. At the threshold of a major breakthrough", Radiographies, 20: 9-27 (2000).
Drognitz, O., et al., Abstract of "Release of vancomycin and teicoplanin from a plasticized and resorbable gelatin sponge: in vitro investigation of a new antibiotic delivery system with glycopeptides"; Indection Germany (Minich); 34(1): 29-34 (2006).
Duchene, D., et al., "Pharmaceutical and Medical Aspects of Bioadhesive Systems for Drug Administration," Drug Dev and Industr Pharmacy, 14(2&3):283-318 (1988).
Edgerton, M., et al., "Vascular Hamatomas and Hemagiomas: Classification and Treatment," Southern Medical Journal, 75(12): 1541-1547 (1982).
Ellegala, D.B., et al., "Use of FloSeal Hemostatic Sealant in Transsphenoidal Pituitary Surgery: Technical Note."; Neurosurgery, 51: 513-516 (Aug. 2002).
English Derwent Abstract of Ranjane reference, Nov. 18, 1997.
Filippi, R., et al., "Bovine Pericardium for Duraplasty: Clinical Results in 32 Patients," Neurological Review, 20:103-107 (2001).
Final Office Action for U.S. Appl. No. 14/136,578, titled: "Device for Promotion of Hemostasis and/or Wound Healing", dated Feb. 26, 2015 "Dry Haemostatic Composition".
Final Office Action for U.S. Appl. No. 14/136,578, titled: "Device for Promotion of Hemostasis and/or Wound Healing", dated Oct. 29, 2015.
Final Office Action for U.S. Appl. No.: 14/383,461, titled: "Pressurized Container Containing Haemostatic Paste", dated Dec. 14, 2017.
Fiss, I., et al., "Use of Gelatin-Thrombin Hemostatic Sealant in Cranial Neurosurgery," Neurologia Medico-Chirurgica, 47(10):462-467 (2007).
Flory, P., "Phase Equilibria in Polymer Systems," Principles of Polymer Chemistry, 13: 541-594 (1953).
FloSeal Matrix Hemostatic Sealant, Instructions for Use, Retrieved from Internet URL http://www.ctsnet.org/file/vendors/931/pdf/140.pdf [retrieved on Aug. 17, 2005].
Fujii, Y., et al., "Safety of GT XIII (Report 2)—Japanese + English translation," The Clinical Report, 20(17) (Dec. 1986).
Gall, R.M., "Control of Bleeding in Endoscopic Sinus Surgery: Use of a Novel Gelatin-Based Hemostatic Agent", Journal of Otolaryngology, 31(5): (2002).
Gelfoam absorbable powder. Retrieved from Internet URL: http://www.fda.gov/cdrh/pdf/N18286S012c.pdf [retrieved on May 22, 2009].
Gibble, J.W., et al., "Fibrin glue: the perfect operative sealant?" Reviews: Transfusion, 30(8): 741-747 (1990).
Guinto, F., "Preparation of Gelfoam Particles Using an Orthopedic Rasp," Radiology, 153: 250 (1984).
Gurny, R., et al.,"Bioadhesive Intraoral Release Systems: Design, Testing and Analysis," Biomaterials, 5: 336-340 (1984).
Hae-Won, K., et al., Abstract of "Porus scaffolds of gelatin-hydroxyapatite nanocomposites obtained by biometic approach: Characterization and antibiotic drug release."; J. of Biomedical Materials Research, 74B(2): 686-698 (2005).
Harris, W.H., et al., "Topical Hemostatic Agents for Bone Bleeding in Humans," The Journal of Bone and Joint Surgery, 60-A(4): 454-456 (1978).
Heller, J., et al., "Release of Norethindrone from Poly(Ortho Esters)," Polymer Engineering and Science, 21: 727-731 (1981).
Herndon, J., et al., "Compression of the Brain and Spinal Cord Following Use of Gelfoam," Arch. Surg, 104: 107 (Jan. 1972).
Hieb, L., et al, "Spontaneous Postoperative Cerebrospinal Fluid Leaks Following Application of Anti-Adhesion Barrier Gel," Spine, 26(7): 748-751 (2001).
Hill, et al., "Use of microfibrillar collagen hemostat (avitenet) and thrombin to achieve hemostats after median sternotomy."; J. Thorac Cardiovasc Surg., 108: 1151-1152 (1994).
Hill-West, J.L., et al., "Efficacy of a resorbable hydrogel barrier, oxidized regenerated cellulose and hyaluronic acid in the prevention of ovarian adhesions in a rabbit model."; Fertility and Sterility, 62(3): 630-634 (1994).
Hong, S.R., et al., Abstract of "Study on gelatin-containing artificial skin IV: a comparative study on the effect of antibiotic and EGF on cell proliferation during epidermal healing."; Biomaterials, 22(20): 2777-2783 (2001).
Hong, Y.M., et al., "The Use of Hemostatic Agents and Sealants in Urology", The Journal of Urology, 176: 2367-2374 (2006).
Hood, D., et al., "Efficacy of Topical Hemostat Floseal Matrix in Vascular Surgery," 24th World Congress of the International Society for Cardiovascular Surgery, Sep. 12-16, 1999, 2 pages.
Hotz, G., et al., "Collagen and Fibrin as Biologic Binders from Granular Hydroxyapatite," Deutsche Zeitschrift fur Mund-Kieferund Gesichts-Chirurgie, 13(4): 296-300 (1989). Abstract retrieved from http://www.ncbi.nlm.nih.gov on Jan. 3, 2001.
International Preliminary Examination Report for International Application No. PCT/DK03/00855, "Gelatine-Based Materials as Swabs", completed Jun. 2, 2005.
International Preliminary Report on Patentability (Corrected Version) for International Application No. PCT/DK2005/000063, "Haemostatic Sprays and Compositions", completed Nov. 6, 2006.
International Preliminary Report on Patentability for International Application No. PCT/DK2005/000475, "Haemostatic Composition Comprising Hyaluronic Acid", completed Aug. 16, 2006.
International Preliminary Report on Patentability for International Application No. PCT/DK2007/050196, "Wound or Tissue Dressing Comprising Lactic Acid Bacteria", completed May 29, 2009.

(56) References Cited

OTHER PUBLICATIONS

International Preliminary Report on Patentability for International Application No. PCT/DK2009/050048, "Device for Promotion of Hemostasis and/or Wound Healing", completed Sep. 6, 2010.
International Preliminary Report on Patentability for International Application No. PCT/DK2013/050054, "Pressurized Container Containing Haemostatic Paste", dated Sep. 9, 2014.
International Preliminary Report on Patentability from counterpart International Application No. PCT/DK2011/050082, "A Method for Promotion of Hemostasis and/or Wound Healing", dated Jul. 6, 2012.
International Search Report & Written Opinion of the International Searching Authority for International Application No. PCT/DK2007/050196, "Wound or Tissue Dressing Comprising Lactic Acid Bacteria", dated Apr. 23, 2008.
International Search Report and Written Opinion of the International Searching Authority from counterpart International Application No. PCT/DK2011/050082, "A Method for Promotion of Hemostasis and/or Wound Healing", dated Jun. 21, 2011.
International Search Report for International Application No. PCT/DK2003/000855, "Gelatine-Based Materials as Swabs", dated Oct. 8, 2004.
International Search Report for International Application No. PCT/DK2005/000063, "Haemostatic Sprays and Compositions", dated Jul. 28, 2005.
International Search Report for International Application No. PCT/DK2005/000475, "Haemostatic Composition Comprising Hyaluronic Acid", dated Oct. 25, 2005.
International Search Report for International Application No. PCT/DK2009/050048, "Device for Promotion of Hemostasis and/or Wound Healing", dated Apr. 6, 2010.
International Search Report for International Application No. PCT/DK2013/050054, "Pressurized Container Containing Haemostatic Paste", dated Sep. 10, 2013.
International Search Report for International Application No. PCT/DK2013/050191, "Dry Haemostatic Composition", dated Aug. 21, 2013.
Jeong, B., et al., "Biodegradable Block Copolymers as Injectable Drug-Delivery Systems," Nature, 388: 860-862 (1997).
Jonas, R., et al., "A new sealant for knitted Dacron prostheses: Minimally cross-linked gelatin," Journal of Vascular Surgery, 7(3): 414-419 (1988).
Katayama, T., et al., "GT XIII safety (3rd report)—Japanese + English translation," The Clinical Report, vol. 20 (1986).
Kelly M.J. et al., "The value of an operative wound swab sent in transport medium in the prediction of later clinical wound infection: A controlled clinical and bacteriological evaluation.", Brit. J. Surgery, 65: 81-88 (1978).
Kim, K., et al., "Reduction in Leg Pain and Lower-Extremity Weakness with Oxiplex/SP Gel for 1 Year after Laminevtomy, Laminotomy, and Disectomy," Neurosurgical Focus, 17: 1-6 (2004).
Kline, D., et al., "Dural Replacement with Resorbable Collagen," Archives of Surgery, 91: 924-929 (1965).
Knopp, U., "A New Collagen Foil Versus a Cadaveric Dura Graft for Dural Defects—A Comparative Animal Experimental Study," European Association of Neurosurgical Societies—Proceedings of the 12th European Congress of Neurosurgery, Lisbon, 17 pages. (2003).
Koçak, I., et al., "Reduction of adhesion formation with cross-linked hyaluronic acid after peritoneal surgery in rats.", Fertility and Sterility, 72(5): 873-878 (1999).
Kofidis, T., et al., "Clinically Established Hemostatis Scaffold (Tissue Fleece) as Biomatrix in Tissue and Organ Engineering Research," Tissue Engineering, 9: 517-523 (2003).
Kost J., and Langer R., "Equilibrium Swollen Hydrogels in Controlled Release Applications," Ch. 5: Hydrogels in Medicine and Pharmacy, vol. III: properties and Applications, N. Peppas ed., pp. 95-108 (1987).

Krill, D., et al., "Topical Thrombin and Powdered Gelfoam: An Efficient Hemostatic Treatment for Surgery," Journal of Tennessee Dental Association, 66(2): 26-27 (1986).
Kuhn, J., et al., "Bilateral Subdural Heamatomata and Lumbar Pseudomeningocele Due to a Chronic Leakage of Liquor Cerebrospinalis after a Lumbar Disectomy with the Application of ADCON-L Gel," Journal of Neurology, Neurosergery & Psychiatry, 76: 1031-1033 (2005).
Langer, R., et al., "Chemical and Physical Structure of Polymers as Carriers for Controlled Release of Bioactive Agents: A Review," Journal of Macromolecular Science-Reviews in Macromolecular Chemistry and Physics, C23: 61-126 (1983).
Laquerriere, A., et al., "Experimental Evaluation of Bilayered Human Collagen as a Dural Substitute," Journal of Neurosurgery, 78: 487-491 (1993).
Larson, P., "Topical Hemostatic Agents for Dermatologic Surgery," Journal of Dermatologic Surgery & Oncology, 14: 623-632 (1988).
Larsson, B., et al., "Surgicel®—an absorbable hemostatic material—in prevention of peritoneal adhesion in rats."; Acta Chir Scand., 26(144): 375-378 (1978).
Laurent, C., et al., "Hyaluronic acid reduces connective tissue formation in middle ears filled with absorbable gelatin sponge: An experimental study.", Am. J.Otolaryngol, 7: 181-186 (1986).
Le, A., et al., "Unrecognized Durotomy After Lumbar Discectomy: A Report of Four Cases Associated with the Use of ADCON-L," Spine, 26(1): 115-118 (2001).
Lee, J., et al., "Experimental Evaluation of Silicone-Coated Dacron and Collagen Fabric-Film Laminate as Dural Substitutes," Journal of Neurosurgery, 27: 558-564 (1967).
Lee, P., "Interpretation of Drug-Release Kinetics from Hydrogel Matrices in Terms of Time-Dependent Diffusion Coefficients," Controlled-Release Technology—Pharmaceutical Applications, Ch. 5, ACS Symposium Series 348, pp. 71-83 (1986).
Leong, K., et al., "Polyanhydrides for Controlled Release of Bioactive Agents," Biomaterials, 7: 364-371 (1986).
Leong, K., et al., "Polymeric Controlled Drug Delivery," Advanced Drug Delivery Reviews, 1: 199-233 (1987).
Lewis, K., et al., "Comparison of Two Gelatin and Thrombin Combination Hemostats in a Porcine Liver Abrasion Model," Journal of Investigative Surgery, 26: 141-148 (2013).
Li, G., et al., "Evaluation of esterified hyaluronic acid as middle ear-packing material.", Arch Otolaryngol Head Neck Surg, 127: 534-539 (2001).
Loeb, J, "The Influence of Electrolytes Upon the Osmotic Pressure of Gelatin Solutions", J. Biol. Chem., 35: 497-508 (1918).
Luengo, J., et al., "Prevention of peritoneal adhesions by the combined use of Spongostan and 32% Dextran 70: An experimental study in pigs." Fertility and Sterility, 29(4): 447-450 (1978).
Masar, E., et al., "Synthesis of Polyurethanes and Investigation of their Hydrolytic Stability," Journal of Polymer Science: Polymer Symposium, 66: 259-268 (1979).
Masuzawa, M., et al., "Experimental Study Related to the Hemostasis Action of GT XIII," The Clinical Report, 20(2): 471-476 (Feb. 1986).
Matsumoto, K., et al., "A Gelatin Coated Collagen—Polyglycolic Acid Composite Membrane as a Dural Substitute," American Society for Artificial Internal Organs Journal, 47: 641-645 (2001).
Maurer, P, et al., "Vicryl (Polyglactin 910) Mesh as a Dural Substitute," Journal of Neurosurgery, 63:448-452 (1985).
Maxson, W.S., et al., "Efficacy of a modified oxidized cellulose fabric in the prevention of adhesion formation." Gynecol. Obstet. Invest., 26: 160-165 (1988).
McClure, J., et al., "Massive Gastroduodenal Hemorrhage: Treatment with Powdered Gelfoam and Buffered Thrombin Solution," Surgery, 32: 630-637 (1952).
McPherson, J., et al., "An Examination of the Biologic Response to Injectable, Glutaraldehyde Cross-linked Collagen Implants," Journal of Biomedical Materials Research, 20: 93-107 (1986).
McPherson, J., et al., "Development and Biochemical Characterization of Injectable Collagen," J. Dermatol. Surg. Oncol., 12(1): 13-20 (Jul. 7, 1988).

(56) References Cited

OTHER PUBLICATIONS

McPherson, J., et al., "The Effects of Heparin on the Physiochemical Properties of Reconstituted Collagen," Collagen and Related Research, 1: 65-82 (1988).
McPherson, J., et al., "The Preparation and Physiochemical Characterization of an Injectable Form of Reconstituted, Glutaraldehyde Crosslinked, Bovine Corium Collagen," Journal of Biomedical Materials Research, 20: 79-92 (1986).
Meddings, N., et al., "Collagen Vicryl—A New Dural Prosthesis," Acta Neurochirurgica, 117: 53-58 (1992).
Mello, L., et al., "Duraplasty with Biosynthetic Cellulose: An Experimental Study," Journal of Neurosurgery, 86: 143-150 (1997).
Miller, D., and Peppas, N., "Diffusional Effects During Albumin Adsorption on Highly Swollen Poly(vinyl Alcohol) Hydrogels," Eur. Polym. J., 24(7): 611-615 (1988).
Miller, E.D., et al., "Dose-Dependent Cell Growth in Response to Concentration Modulated Patterns of FGF-2 Printed on Fibrin," Biomaterials, 27: 2213-2221 (2006).
Millikan, L., "Treatment of Depressed Cutaneous Scars with Gelatin Matrix Implant: A Multicenter Study," J. Am. Acad. Dermatol., 16: 1155-1162 (1987).
Min et al., "Molecular Weight Changes of Sodium Hyaluronate Powder and Solution by Heat treatment," Matrix Biology Institute, Proceedings of Hyaluronan, Oct. 11-16, 2003.
Mitsuhashi, J., "Invertabrate Tissue Culture Methods," Springer Lab Manual, p. 407 (2002).
Moak, E., "Hemostatic Agents: Adjuncts to Control Bleeding," Today's O.R. Nurse, pp. 6-10 (1991).
Mueller, K., "Release and Delayed Release of Water-Soluble Drugs from Polymer Beads with Low Water Swelling," Controlled-Release Technology—Pharmaceutical Applications, Ch. 11, ACS Symposium Series, 348: 139-157 (1986).
Muranyi, et al., "Development of gel-forming lyophilized formulation with recombinant human thrombin", Drug Development and Industrial Pharmacy 41(9): (2015) 1566-1573. (Abstract Only).
Narotam, P., et al., "A Clinicopathological Study of Collagen Sponge as a Dural Graft in Neurosurgery," Journal of Neurosurgery, 82: 406-412 (1995).
Narotam, P., et al., "Experimental Evaluation of Collagen Sponge as a Dural Graft," British Journal of Neurosurgery, 7: 635-641 (1993).
Nimni, M., et al., "Chemically Modified Collagen: A Natural Biomaterial for Tissue Replacement," Journal of Biomedical Materials Research, 21: 741-771 (1987).
Nimni, M., Ph.D., "The Cross-Linking and Structure Modification of the Collagen Matrix in the Design of Cardiovascular Prosthesis," Journal of Cardiac Surgery, 3: 523-533 (1988).
Nogueira, L., et al., Comparison of gelatine matrix-thrombin sealants used during laparoscopic partial nephrectomy, BJU International, 102: 1670-1674 (2008).
Non-Final Office Action for U.S. Appl. No. 14/136,578, titled: "Device for Promotion of Hemostasis and/or Wound Healing", dated Oct. 2, 2014.
Non-Final Office Action for U.S. Appl. No. 14/383,461, titled: "Pressurized Container Containing Haemostatic Paste", dated Jun. 15, 2017.
Non-Final Office Action for U.S. Appl. No. 14/516,728 dated Apr. 14, 2015 "Dry Haemostatic Composition".
Non-Final Office Action for U.S. Appl. No. 14/516,728, titled: "Dry Haemostatic Composition" dated Nov. 25, 2014.
Non-Final Office Action for U.S. Appl. No. 14/980,254, titled: "Dry Haemostatic Composition", dated May 8, 2017.
Notice of Allowability for U.S. Appl. No. 14/895,674, titled: "Vacuum Expanded Dry Composition and Syringe for Retaining Same", dated Jun. 12, 2017.
Notice of Allowance for U.S. Appl. No. 14/136,578, titled: "Device for Promotion of Hemostasis and/or Wound Healing" dated Sep. 23, 2016.
Notice of Allowance for U.S. Appl. No. 14/516,728, titled: "Dry Haemostatic Composition" dated Nov. 27, 2015.

Notice of Allowance for U.S. Appl. No. 14/895,674, titled: "Vacuum Expanded Dry Composition and Syringe for Retaining Same", dated May 30, 2017.
Notification of Transmittal of the International Search Report and the Written Opinion of the International Searching Authority for International Application No. PCT/EP2015/080761, "Syringe for Retaining and Mixing First and Second Substances", dated Feb. 19, 2016.
Novak, D., "Embolization Materials," Interventional Radiology, pp. 295-313 (1990).
O'Neill, P., et al., "Use of Porcine Dermis as a Dural Substitute in 72 Patients," Journal of Neurosurgery, 61: 351-354 (1984).
Office Action for U.S. Appl. No. 14/136,578, titled: "Device for Promotion of Hemostasis and/or Wound Healing", dated Aug. 13, 2015.
Office Action for U.S. Appl. No. 14/895,674, titled: "Vacuum Expanded Dry Composition and Syringe for Retaining Same", dated Feb. 6, 2017.
Ofner, C.M. and Bubnis, W.A., "Chemical and Swelling Evaluations of Amino Group Crosslinking in Gelatin and Modified Gelatin Matrices," Pharma. Res., 13: 1821-1827 (1996).
Oyelese, Yinka, et al., "Postpartum Hemhorrage," Obstetrics and Gynecology Clinics of North America 34.3, 421-441 (2007).
Oz, M.C., et al., "Controlled clinical trial of a novel hemostatic agent in cardiac surgery.", Ann Thorac Surg, 69: 1376-1382 (2000).
Oz, M.C., et al., "Floseal-Matrix: New Generation Topical Hemostatic Sealant", J. Card. Surg., 18: 486-493 (2003).
Palm, S., et al., "Dural Closure with Nonpenetrating Clips Prevents Meningoneural Adhesions: An Experimental Study in Dogs," Neurosurgery, 45(4): 875-882 (1999).
Parizek, J., et al., "Detailed Evaluation of 2959 Allogeneic and Xenogeneic Dense Connective Tissue Grafts (Fascia Lata, Pericardium, and Dura Mater) Used in the Course of 20 Years for Duraplasty in Neurosurgery," Acta Neurochirurgica, 139: 827-838 (1997).
Park, Y-K., et al., "Prevention of Arachnoiditis and Postoperative Tethering of the Spinal Cord with Gore-Tex Surgical Membrane: An Experimental Study with Rats," Neurosurgery, 42(4): 813-824 (1998).
Peppas, N. and Barr-Howell, B., "Characterization of the Cross-Linked Structure of Hydrogels," Ch. 2: Hydrogels in Medicine and Pharmacy, vol. I: Fundamentals, N. Peppas ed., pp. 27-56 (1986).
Peppas, N. and Brannon-Peppas, L, "Hydrogels at Critical Conditions. Part 1. Thermodynamics and Swelling Behavior," Journal of Membrane Science, 48: 281-290 (1990).
Peppas, N. and Khare, A., "Preparation, Structure and diffusional Behavior of Hydrogels in Controlled Release," Adv. Drug Delivery Reviews, 11: 1-35 (1993).
Peppas, N. and Korsmeyer, R, "Dynamically Swelling Hydrogels in Controlled Release Applications," Ch. 6: Hydrogels in Medicine and Pharmacy, vol. III: Properties and Applications, N. Peppas ed., pp. 109-135 (1987).
Peppas, N. and Lustig, S., "Solute Diffusion in Hydrophilic Network Structures," Ch. 3: Hydrogels in Medicine and Pharmacy, vol. I: Fundamentals, N. Peppas ed., pp. 57-83 (1986).
Peppas, N. and Mikos, A., "Preparation Methods and Structure of Hydrogels," Ch. 1: Hydrogels in Medicine and Pharmacy, vol. I: Fundamentals, N. Peppas ed., pp. 1-25 (1986).
Peppas, N. and Moynihan, H, "Structure and Physical Properties of Poly(2-Hydroxyethyl Methacrylate) Hydrogels," Ch. 2: Hydrogels in Medicine and Pharmacy, vol. II: Polymers, N. Peppas ed., pp. 49-64 (1987).
Peppas, N., "Hydrogels and Drug Delivery," Current Opinion in Colloid & Interface Science, 2: 531-537 (1997).
Peppas, N., "Hydrogels in Medicine and Pharmacy," Hydrogels in Medicine and Pharmacy, vol. 1. Fundamentals, CRC Press, Boca Raton, FL, 180 pages (1986).
Peppas, N., "Hydrogels in Medicine and Pharmacy," Hydrogels in Medicine and Pharmacy, vol. 2. Polymers, CRC Press, Boca Raton, FL, 172 pages (1987).
Peppas, N., "Hydrogels in Medicine and Pharmacy," Hydrogels in Medicine and Pharmacy, vol. 3. Properties and Applications, CRC Press, Boca Raton, FL, 196 pages (1987).

(56) References Cited

OTHER PUBLICATIONS

Peppas, N., "Hydrogels of Poly (Vinyl Alcohol) and its Copolymers," Ch. 1: Hydrogels in Medicine and Pharmacy, vol. II: Polymers, N. Peppas ed., pp. 57 pgs (1987).

Peppas, N., ed., "Other Biomedical Applications of Hydrogels," Ch. 9: Hydrogels in Medicine and Pharmacy, vol. III: Properties and Applications, pp. 177-186 (1987).

Pietrucha, K., "New Collagen Implant as Dural Substitute," Biomaterials, 12: 320-323 (1991).

Pitt, C., et al., "Biodegradable Drug Delivery Systems Based on Aliphatic Polyesters: Application to Contraceptives and Narcotic Antagonists," Controlled Release of Bioactive Materials, R. Baker, ed., (NY: Academic Press) pp. 19-43 (1980).

Porchet, F., et al., "Inhibition of Epidural Fibrosis with ADCON-L: Effect on Clinical Outcome One Year Following Reoperation for Recurrent Lumbar Radiculopathy," Neurological Research, 21: 551-560 (1999).

Product leaflet for FloSeal ®Matrix Hemostatic Sealant dated Jul. 2001 (Jul. 2001).

Pschyrembel®—Klinisches Wörterbuch, 261st edition, de Gruyter (2007).

Purdy, P.D., et al., "Microfibrillar collagen model of canine cerebral infarction"; Strokes, 20(10): 1361-1367 (Oct. 1989).

Quintavalla, J., et al., "Fluorescently labeled mesenchymal stem cells (MSCs) maintain mutlilineage potential and can be detected following implantation into Particular cartilage defects.", Biomaterials, 23: 109-119 (2002).

Raftery, A., "Absorbable haemostatic materials and intraperitoneal adhesion formation."; Br. J. Surg. 67; 1980; pp. 57-58.

Ratner, B., "Hydrogel Surfaces," Ch. 4: Hydrogels in Medicine and Pharmacy, vol. I: Fundamentals, N. Peppas ed., pp. 85-94 (1986).

Raul, J.S., et al., "Utilisation du Polyester Urethane (Neuropatch) Comme Substitut Dural," Neurochirugie, 49: 83-89, English abstract only on p. 83 (2003).

Reddy, M., et al., "A Clinical Study of a Fibrinogen-Based Collagen Fleece for Dural repair in Neurosergery," Acta Neurochirurgica, 144: 265-269 (2002).

Reese, A.C., "Role of fibronectin in wound healing", Report date: Sep. 12, 1986; Annual rept. Oct. 1, 1985-Mar. 31, 1986, Final rept. Oct. 1, 1983-Mar. 31, 1986. Corporate Author: Medical Coli of Gerogia Augusta Research Institute. Brunt and Klausner, "Growth factors speed wound healing", Nature Biotechnology, 6(1): 25-30 (1988).

Reijnen, M.M.P.J., et al., "Prevention of intra-abdominal abscesses and adhesions using a hyaluronic acid solution in a rat peritonitis model." Arch Surg. 134: 997-1001 (1999).

Renkens, K., et al, "A Multicenter, Prospective, Randomized Trial Evaluating a New Hemostatic Agent for Spinal Surgery," Spine, 26(15): 1645-1650 (2001).

Riley, S., et al. "Percutaneous Liver Biopsy with Plugging of Needle Track: A Safe Method for Use in Patients with Impaired Coagulation," Lancet, p. 436 (1984).

Roda, A., et al., "Protein Microdeposition Using a Conventional Ink-Jet Printer," BioTechniques, 28(3): 492-496 (2000).

Romanelli, M., et al., "Exudate Management Made Easy", downloaded from http://www.woundsinternational.com, 6 pgs., (Jan. 29, 2010).

Rosenblatt, J., et al., "Effect of Electrostatic Forces on the Dynamic Rheological Properties of Injectable Collagen Biomaterials," Biomaterials, 13: 878-886 (1982).

Rosenblatt, J., et al., "Injectable Collagen as a pHSensitive Hydrogel," Biomaterials, 12: 985-995 (1984).

Ross, J., et al., "Association Between Peridural Scar and Recurrent Radicular Pain After Lumbar Discectomy: Magnetic Resonance Evaluation," Neurosurgery, pp. 855-863 (1996).

Rossler, B., et al., "Collagen Microparticles: Preparation and Properties," Journal of Microencapsulation, 12: 49-57 (1995).

Sakurabayashi, S., et al., "Clinical evaluation of new hemostatic agent for hemostasis from biopsy wounds in the liver."; Gastroenterological Endoscopy 30:(10) 29 pgs. (Oct. 1988).

Sanfilippo, J.S., et al., "Comparison of avitene, topical thrombin and Gelfoam as sole hemostatic agent in tuboplasties.", Fertility and Sterility, 33(3): 311-316 (1980).

San-Galli, F., et al., "Experimental Evaluation of a Collagen-Coated Vicryl Mesh as a Dural Substitute," Neurosurgery, 30: 396-401 (1992).

Santomaso, A., et al., "Powder flowability and density rations: the impact of granules packing", Chemical Engineering Science, 58: 2857-2874 (2003).

Schramm, V., et al., "Gelfoam Paste Injection for Vocal Cord Paralysis," The Laryngoscope, 88: 1268-73 (1978).

Schreiber, M.A., et al., "Achieving Hemostasis with Topical Hemostats: Making Clinically and Economically Appropriate Decisions in the Surgical and Trauma Settings", AORN Journal, 94(5): S1-S20 (2011).

Shaffrey, C.I., et al., "Neurosurgical Applications of Fibrin Glue: Augmentation of Dural Closure in 134 Patients," Neurosurgery, 26: 207-210 (1990).

Shushan, A., et al., "Hyaluronic acid for preventing experimental postoperative intraperitoneal adhesions.", Journal of Reproductive Medicine, 39(5): 398-402 (1994).

Shuxian, M. and Zhili, C., "Clinical Observation of the Treatment of Hemoptysis by Ultrasonic Atomizing Inhalation of Thrombin", Chinese Journal of Critical Care Medicine, 16(2): 30 (1996).

Sidman, K., et al., "Biodegradable, Implantable Sustained Release Systems Based on Glutamic Acid Copolymers," Journal of Membrane Science, 7: 227-291 (1979).

Sigma-Aldrich Datasheet for "Hank's Balanced Salts," revised Apr. 2007.

Simamora, P., et al., "Controlled delivery of pilocarpine. 2. In-vivo evaluation of Gelfoam® device," International Journal of Pharmaceutics, 170(2): 209-214 (1998).

Smith, A., "New and Nonofficial Remedies: Absorbable Gelatin Sponge—Gelfoam-Upjohn," Council on Pharmacy and Chemistry, 135(14): p. 921 (1947).

Smith, K., et al., "Delayed Postoperative Tethering of the Cervical Spinal Cord," Journal of Neurosurgery, 81: 196-201 (1994).

Solar Biologicals Inc., "Solar-cult sampling products: Pre-moistened cellulose sponge sampling systems", available at www.solarbiologicals.com/samp-sys.htm (Jul. 25, 2002).

Soules, M.R., et al., "The prevention of postoperative pelvic adhesions: An animal study comparing barrier methods with Dextran 70.", Am. J. Obstet. Gynecol., 143(7): 829-834 (1982).

Spence et al., "Cerebellar capillary hemangioblastoma: its histogenesis studied by organ culture and electron microscopy.", Cancer, 35(2): 326-341 (Feb. 1975).

Spotnitz, W. D., et al., "Hemostatus, Sealants, and Adhesives: Components of the Surgical Toolbox," Transfusion, 48(7):1502-1516 (2008).

Springorum, H., "Die Verwendung von Kollagenfolien Zur Uberbruckung von Defekten des Gleitgewebes bei Achillotenotomien and Achillessehnenrupturen," Akt. Traumatol., 15: 120-121, English abstract only on p. 120 (1985).

Stief, T. W., "Kallikrein Activates Prothrombin," Clinical and Applied Thrombosis/Hemostasis, 14.1:97-98 (2008).

Stricker, A., et al., "Die Verwendung von TissuFoil Membran bei der Sinusbodenaugmentation," Ellipse, 17: 1-5 (2001). English abstract only on p. 1.

Stuart Transport medium information sheet [retrieved online on May 27, 2009].

Sugitachi, A., et al., "A Newly Devised Chemo-Embolic Agent, G.T. XIIIADM," Gan. To. Kagaku Ryoho, 12: 1942-1943 (1985). English abstract retrieved from http://www.ncbi.nlm.nih.gov on Jan. 2, 2001.

Sugitachi, A., et al., "Locoregional Therapy in Patients with Malignant Pleural Effusion—Two Different Kinds of 'BAC Therapy'," Gan. To. Kagaku Ryoho, 19: 1640-1643 (1992). English abstract retrieved from http://www.ncbi.nlm.nih.gov on Jan. 3, 2001.

Sugitachi, A., et al., "Preoperative Transcatheter Arterial Chemo—Embolization for Locally Advanced Breast Cancer: Application for New Thrombotic Materials." Japanese Journal of Surgery, 13: 456-458 (1992).

(56) References Cited

OTHER PUBLICATIONS

Surgiflo® Essential Prescribing Information, Hemostatic Matrix (Made from Absorbable Gelatin Sponge, U.S.P.), 1 page (2005).
Surgiflo® haemostatic matrix FlexTip, MS0009, 84 pages (2007).
Surgiflo® product leaflet, "Surgiflo® Hemostatic Matrix Kit," 5 pages (2012).
Surgiflo® product leaflet, "Surgiflo® Hemostatic Matrix," 12 pages (2009).
Swann, D.A.," Studies on hyaluronic acid-I. The preparation and properties of rooster comb hyaluronic acid", Biochemica et biophysica acta, 156: 17-30 (1968).
Taheri, Z., "The Use of Gelfoam Paste in Anterior Cervical Fusion," Journal of Neurosurgery, 34: 438 (1971).
Tobin, M., et al., "Plugged Liver Biopsy in Patients with Impaired Coagulation," Digestive Diseases and Science, 34: 13-15 (1989).
Tucker, H., "Absorbable Gelatin (Gelfoam) Sponge," Springfield, Illinois, Charles T. Thomas, pp. 3-125 (1965).
Van den Bosch, E., et al., "Gelatin degradation at elevated temperature", International Journal of Biological Macromolecules, 32: 129-138 (2003).
Vandelli, M.A., et al., "The effect of the crosslinking time period upon the drug release and the dynamic swelling of gelatin microspheres," Pharmazie, 46: 866-869 (1991).
Vander-Salm, T.J., et al., Abstract of "Reduction of sternal infection by application of topical vancomycin.", J. of Thoracic and Cardiovascular Surgery, 98(4): 618-622 (1989).
Verhoeven, A.G., et al., "XV. The use of microporous polymeric powders for controlled release drug delivery systems," Controlled Drug Delivery. Ch. 15, International Symposium of the Association for Pharmaceutical Technology (APV), Bad Homburg, Nov. 12-14, 1984, pp. 226-237.
Vinas, F., et al., "Evaluation of Expanded Polytetrafluoroethylene (ePTFE) versus Polydioxanone (PDS) for the Repair of Dura Mater Defects," Neurological Research, 21: 262-268 (1999).
Wachol-Drewek, Z., et al., "Comparative investigation of drug delivery of collagen implants saturated in antibiotic solutions and a sponge containing gentamicin.", Biomaterials, 17: 1733-1738 (1996).
Wallace, D., "The Relative Contribution of Electrostatic Interactions to Stabilization of Collagen Fibrils," Biopolymers, 29: 1015-1026 (1990).
Wallace, D., et al., "Injectable Cross-Linked Collagen with Improved Flow Properties," Journal of Biomedical Materials Research, 23: 931-945 (1989).
Warren, W., et al., "Dural Repair Using Acellular Human Dermis: Experience with 200 Cases: Technique Assessment," Neurosurgery, 46: 1391-1396 (2000).
Wassersug, J.D., M.D., "Use of Human Thrombin in Some Cases of Pulmonary Hemorrhage" Pulmonary Hemorrhage, vol. XVII, pp. 354-356 (Mar. 1950).
Weeks, R., "Microscopy of Soft Materials," Chapter 1 in Experimental and Computational Techniques in Soft Condensed Matter Physics, Jeffrey Olafsen, Ed, 2010 (2010).
West et al., "Efficacy of adhesion barriers: Resorbable hydrogel, oxidized regenerated cellulose and hyaluronic acid.", The Journal of Reproductive Medicine, 41(3) 149-154 (1996).
Wiesenthal, A.A., et al., Abstract of "New method for packing the external auditory canal, middle ear space, and mastoid cavities after otologic surgery", The Journal of Otolaryngology; 28(5): 260-265 (1999).
Wilkinson, H., et al., "Gelfoam Paste in Experimental Laminectomy and Cranial Trephination," Journal of Neurosurgery, 54: 664-667 (1981).
Written Opinion for International Application No. PCT/DK2003/000855, "Gelatine-Based Materials as Swabs", dated Feb. 28, 2005.
Written Opinion of the International Preliminary Examining Authority for counterpart International Application No. PCT/DK2011/050082, "A Method for Promotion of Hemostasis and/or Wound Healing", dated Mar. 23, 2012.

Written Opinion of the International Searching Authority (Corrected Version) for International Application No. PCT/DK2005/000063, "Haemostatic Sprays and Compositions", dated Jul. 26, 2005.
Written Opinion of the International Searching Authority for International Application No. PCT/DK2005/000475, "Haemostatic Composition Comprising Hyaluronic Acid", dated Oct. 24, 2005.
Written Opinion of the International Searching Authority for International Application No. PCT/DK2009/050048, "Device for Promotion of Hemostatis and/or Wound Healing", completed Aug. 31, 2010.
Wu, Y. et al., Abstract of "Design and experimental study of a slow-release antibiotic membrane implant in surgery wound.", Intern. Des Services de San. Des Forces Armees; 72(7-9): 194-196 (Sep. 1999).
Xing, Q., et al., "Increasing Mechanical Strength of Gelatin Hydrogels by Divalent Metal Ion Removal", Sci. Rep., 4: 4706: DOI:10.1038/srep04706(2014).
Xu, T., et al., "Viability and electrophysiology of neural cell structures generated by the inkjet printing method", Biomaterials, 27: 3580-3588 (2006).
Xu, T., et al., "Inkjet Printing of Viable Mammalian Cells," Biomaterials, 26: 93-99 (2005).
Yaping, G., "Observation and Nursing of the Treatment of Hemoptysis of Pulmonary Tuberculosis by Ultrasonic Atomizing Inhalation of Thrombin", Journal of Qilu Nursing, 10(2): 126 (Feb. 2004).
Youwen, W. et al., "Clinical Observation of the Therapeutic Efficacy of the Treatment of 15 Patients with Hemoptysis by Ultrasonic Atomizing Inhalation of Thrombin", Chengdu Medical Journal, 30(5): 262 (Oct. 2004).
Yuki, N., et al., "Effects of Endoscopic Variceal Sclerotherapy Using GT XIII on Blood Coagulation Tests and the Renal Kallikrein-Kinin System," Gastroentral. Japan, 25: 561-567 (1990). English abstract retrieved from http://www.ncbi.nlm.nih.gov [retrieved on Jan. 2, 2001].
Ziegelaar, B., et al., "The Characterisation of Human Respiratory Epithelial Cells Cultured on Resorbable Scaffords: First Steps Towards a Tissue Engineered Tracheal Replacement," Biomaterials, 23: 1425-1438 (2002).
Ziegelaar, B., et al., "Tissue Engineering of a Tracheal Equivalent, Doctoral Thesis," Munich, Germany, Ludwig Maximilians University, 2004, 25 pages (2004).
Zins, M., et al., "US-Guided Percutaneous Liver Biopsy with Plugging of the Needle Track: A Prospective Study in 72 High-Risk Patients," Radiology, 184: 841-843 (1992).
Notice of Allowance for U.S. Appl. No. 14/895,674, titled: "Dry Haemostatic Composition", dated Jan. 24, 2018.
Notification of Transmittal of the International Search Report and the Written Opinion of the International Searching Authority for International Application No. PCT/EP2016/065260, "Syringe for Mixing Two Components and for Retaining a Vacuum in a Storage Condition", dated Oct. 4, 2016.
International Preliminary Report on Patentability for International Application No. PCT/EP2016/065260, "Syringe for Mixing Two Components and for Retaining a Vacuum in a Storage Condition", date of completion Dec. 6, 2017.
Notice of Allowance for U.S. Appl. No. 15/534,801, "Syringe for Retaining and Mixing First and Second Substances", dated Jul. 25, 2019.
Notice of Allowance for U.S. Appl. No. 15/534,801, titled: "Syringe for Retaining and Mixing First and Second Substances", dated Jan. 16, 2020.
Notice of Allowance for U.S. Appl. No. 15/639,237, titled: "Vacuum Expanded Dry Composition and Syringe for Retaining Same", dated Nov. 27, 2019.
Office Action for U.S. Appl. No. 15/963,795, titled: "Dry Haemostatic Composition", dated Feb. 20, 2020.

\* cited by examiner

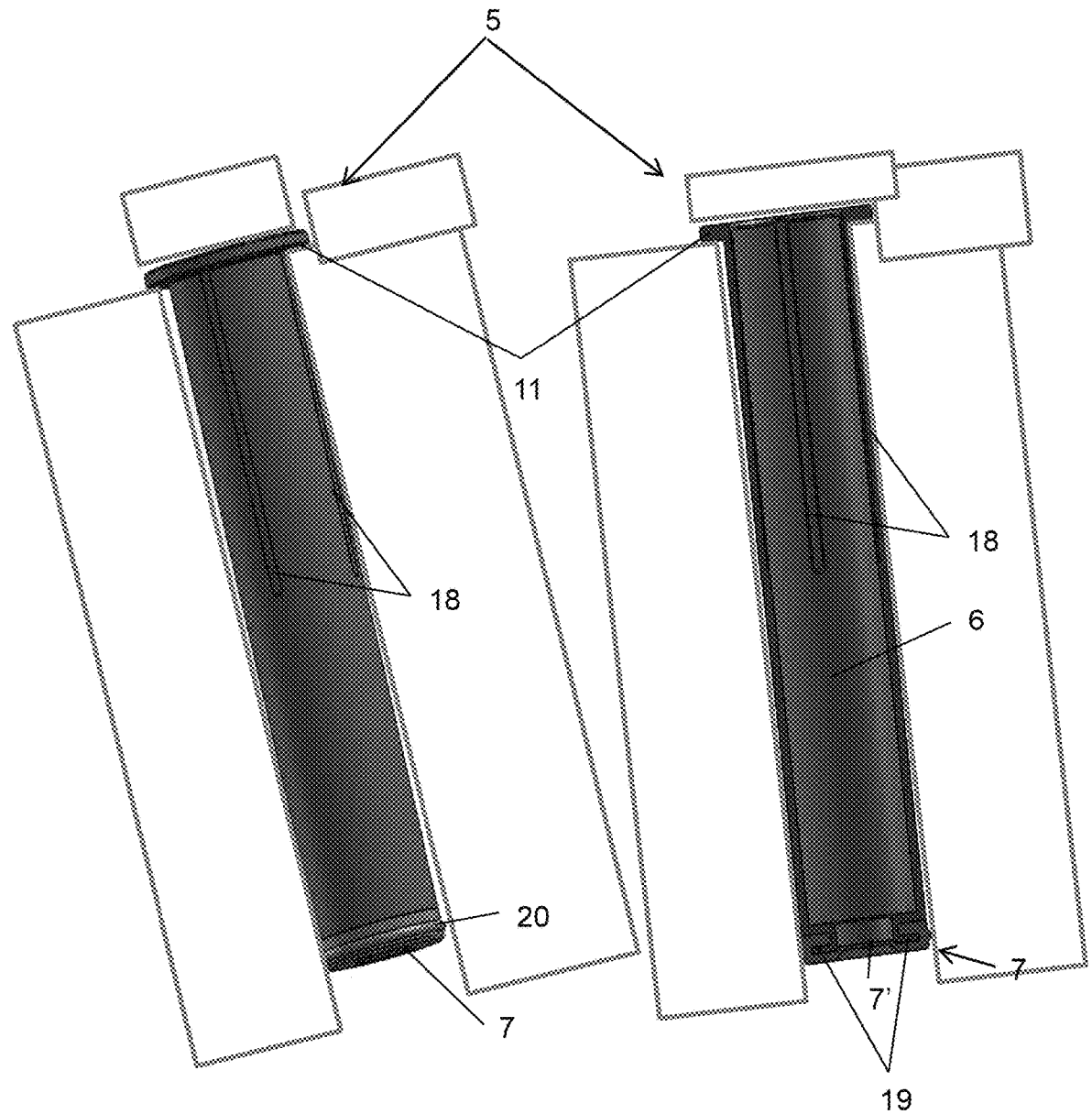

SYRINGE FOR MIXING TWO COMPONENTS AND FOR RETAINING A VACUUM IN A STORAGE CONDITION

This application is the U.S. National Stage of International Application No. PCT/EP2016/065260, filed Jun. 30, 2016, which designates the U.S., published in English, and claims priority under 35 U.S.C. §§ 119 or 365(c) to EP Application No. 15175189.8, filed Jul. 3, 2015. The entire teachings of the above applications are incorporated herein by reference.

FIELD OF INVENTION

The present disclosure relates to a syringe for mixing two substances which have been retained separately inside the syringe, for instance in a storage condition. In particular the present disclosure relates to a syringe for 1) retaining a dry composition in a vacuum, and 2) mixing the dry composition with an aqueous medium to form a flowable substance.

BACKGROUND OF INVENTION

Mixing procedures and manipulations of different substances can be time consuming. Some types of medication are provided and stored in two separate chambers. Such medication may include a solid component and a liquid solvent and are known as two-part formulations. The solid component can be for example a powdered medicament. The substances can also include two liquid substances and/or two medicaments. Before the medicament is delivered, the components have to be mixed.

A syringe can generally be seen as a simple pump device consisting of a plunger in a tube, used to administer injections, insert intravenous drugs or apply compounds. There are a number of syringes capable of mixing and delivering two substances, including autoinjectors. In some of these syringes there are two chambers and a mechanism for mixing the substances either in one of the chambers or in a third chamber, before the mix is delivered, typically through a needle.

U.S. Pat. No. 4,048,999 shows a two-chamber syringe for medicinal purposes having one chamber for a liquid and one container for a solid or another liquid. The syringe has a stopper with an axial bore connecting the syringe to a vial and a second stopper sealing the axial bore and adapted to be ejected with the liquid in the syringe into the container by inward activation of the piston of the syringe.

It can be considered to be known in the art to include an inner needle in the syringe capable of transferring one component from one chamber to the other, thereby mixing the components. WO 2010/020800 A1 shows an autoinjector with mixing means, having a first and a second chamber for two different components. The autoinjector comprises both an injection needle and an internal transfer needle, wherein the transfer needle is capable of penetrating the stopper inside the autoinjector to establish fluid connection through the needle and mix the two components before they are injected.

The known syringes with several chambers and means for mixing several components are associated with a number of disadvantages. The mixing and injection are typically dependent on a manual movement lacking precise control or uses electrical power to control the mixing and injection. These designs are often overly complex and require precise finishing in order to work.

SUMMARY OF INVENTION

The present disclosure relates to a syringe for retaining and mixing first and second substances comprising a barrel comprising a sealable and/or closable distal outlet and a vacuum chamber for holding a first substance. The syringe preferably comprises a plunger, said plunger preferably incorporating a reservoir chamber for holding a second substance. The plunger may be configured to be axially displaced through a proximal end of the barrel. The syringe preferably comprises a membrane separating the vacuum chamber and the reservoir chamber. A pointed member, such as one or more needles, may be provided as part of the syringe suitable for penetrating the membrane. The syringe is preferably configured such that the membrane and the pointed member are axially slidable in relation to each other, preferably in correspondence with an axial displacement of the barrel relative to the plunger. I.e. the syringe is preferably configured such that an axial displacement of the plunger relative to the barrel corresponds to an axial displacement of the membrane and the pointed member relative to each other. For example if the membrane is attached to the plunger and the pointed member is attached to the barrel or vice versa.

The syringe may be configured such that an axial displacement of the plunger from a first position to a predefined second position in the barrel penetrates the membrane by the pointed member and establishes a fluid passageway between the reservoir chamber and the vacuum chamber. Preferably the vacuum in the vacuum chamber thereby aspirates the second substance into the vacuum chamber; the vacuum in the vacuum chamber thereby causing a transfer of the content of the reservoir chamber into the vacuum chamber, preferably without displacement of the plunger from said predefined second position. I.e. the reservoir chamber is thereby emptied or nearly emptied.

One advantage of the presently disclosed syringe is that a reservoir chamber is incorporated in the plunger for holding the second substance. Using the space inside the plunger to store one of the components makes the syringe more compact and lighter. The fact that the plunger is the movable part of the syringe (in relation to the barrel) can also render the design simple in that it is possible to mount the pointed member on the barrel, which is generally more stable than having the needle as a moving part.

Another advantage of the presently disclosed syringe is the vacuum chamber in the barrel for holding a first substance. If vacuum is created in the vacuum chamber, the vacuum may be utilized to move the plunger towards/inside the vacuum chamber and to aspirate the second substance from the reservoir chamber to the vacuum chamber. By first applying vacuum in the vacuum chamber and then letting the vacuum 1) pull the plunger, and 2) draw the content of the reservoir chamber into the vacuum chamber whereby the substances are mixed, the mixing process can be provided in a very controlled and automatic manner without involving manual force or manual movement of the plunger. If the parts of the plunger are produced in a process in which the parts always have the same size and shape, and the vacuum generation is applied in the same way, it can also be expected that the mixing will be performed in the same way every time.

The pointed member suitable for penetrating the membrane, wherein the syringe is configured such that the membrane and the pointed member are axially slidable in relation to each other, is another advantage of the presently disclosed syringe. If the needled is attached to the barrel and axially slidable in relation to the pointed member (which may be part of the plunger, constituting a separating barrier between the two chambers), the vacuum in the vacuum chamber may be used to move the plunger towards the vacuum chamber, the pointed member thereby penetrating the member and providing a fluid connection between the two chambers.

The combination of several of the abovementioned features can also be considered to further improve the design, which can be used with a range of additional mechanisms in order to make use of the invention. For example, the syringe may further comprise different kind of locking members to control the axial positions of the plunger inside the barrel. If vacuum is applied inside the vacuum chamber a mechanical locking mechanism can ensure that the plunger is not moved towards the vacuum chamber until the user removes the lock.

Furthermore, an axially slidable plug inside the plunger can be used to limit the reservoir chamber in the plunger. The syringe can be configured such that the plug slides distally inside the plunger when the substance in the reservoir chamber is transferred to the vacuum chamber. The plug can furthermore be used to plug the fluid connection between the two chambers when the substance of the reservoir of the first chamber has been transferred to the vacuum chamber. Preferably the plug is made of a material that can also be penetrated by the pointed member. Since, in one embodiment, the pointed member protrudes through the membrane after having penetrated the membrane, in a preferred embodiment the plug is made of a material that can also be penetrated by the pointed member, which allows that the plug is aspirated by the vacuum of the vacuum chamber to a position in which it abuts the distal end of the plunger or the member.

These and other aspects of the invention are set forth in the following detailed description if the invention.

DESCRIPTION OF DRAWINGS

FIG. 3A shows an illustration of an exemplary plunger of the presently disclosed syringe.

FIG. 3B shows a cross-sectional illustration of the plunger in FIG. 3A.

Figure 1A:
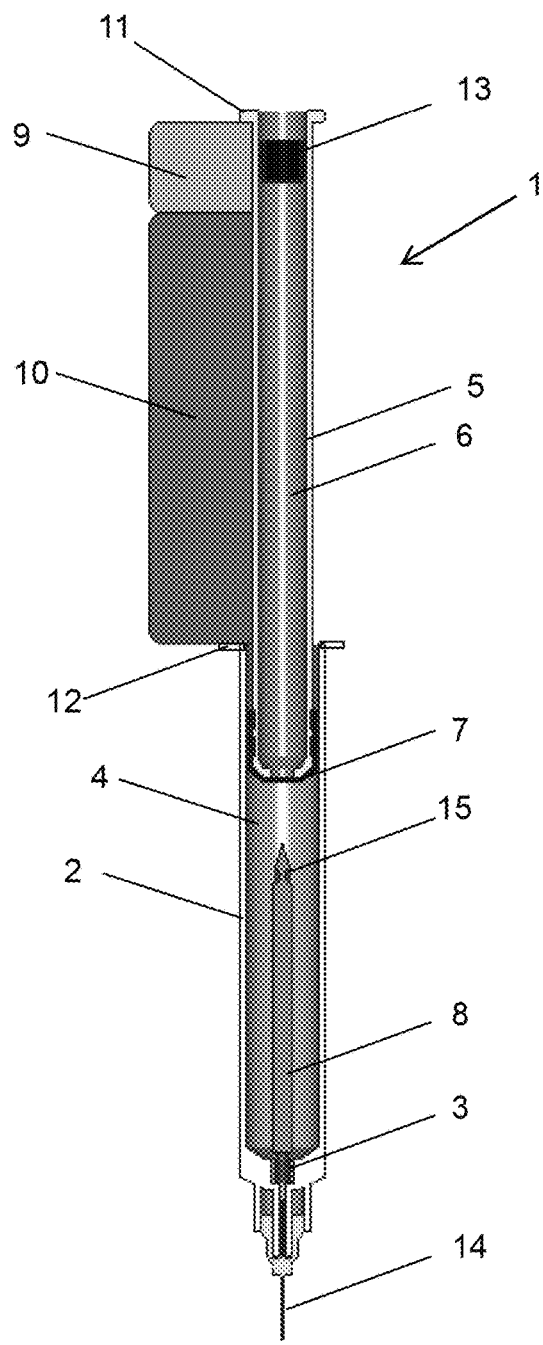
FIG. 1A shows a cross-sectional illustration of one embodiment of the presently disclosed syringe with first and second locking elements, retaining vacuum in the vacuum chamber in a first configuration.

The drawings are exemplary only and should not be construed as limiting the scope of the invention.

Definitions

"Ambient pressure" is herein used interchangeably with the term "atmospheric pressure". It is the pressure in the surrounding area, i.e. the pressure in the location in which a process takes place.

A "reduced pressure" is a pressure below ambient pressure, i.e. a pressure below that of the pressure in the surrounding area in which a certain process operates.

"Vacuum" is herein defined as a region with a gaseous pressure less than the ambient pressure, i.e. the surrounding atmospheric pressure. At sea level on Earth the atmospheric pressure is approximately 1 bar, i.e. 1000 mbar at 25° C. The below table shows the approximate pressures in "low", "medium" and "high" vacuum at sea level on earth in millibar (mbar).

|  | pressure (mbar) |
|---|---|
| Atmospheric pressure | 1000 |
| Low vacuum | 1000 to 100 |
| Medium vacuum | 100 to 0.001 |
| High vacuum | <0.001 |

DETAILED DESCRIPTION OF THE INVENTION

As stated the present disclosure relates to a syringe for retaining and mixing first and second substances comprising a barrel comprising a sealable and/or closable distal outlet and a vacuum chamber for holding a first substance, a plunger incorporating a reservoir chamber for holding a second substance and configured to be axially displaced through a proximal end of the barrel, a membrane separating the vacuum chamber and the reservoir chamber, and a pointed member, such as one or more needles, for penetrating the membrane, wherein the syringe is configured such that the membrane and the pointed member are axially slidable in relation to each other.

By incorporating the plunger in the reservoir chamber, the syringe can be made more compact and lighter compared to a solution in which the barrel contains two chambers for separates substances. In one embodiment the reservoir chamber is completely contained in the plunger, and/or wherein the reservoir chamber is at least partly defined by outer walls of the plunger. Preferably the reservoir chamber is a closed volume within the walls of the plunger, possible having a lid or cap, alternatively having a plug inside the hollow plunger. In one embodiment the reservoir chamber is defined by a hollow portion of the plunger.

The syringe is preferably configured such that the membrane and the pointed member are axially slidable in relation to each other. The idea is that a membrane keeps the two substances in separate containers (i.e. reservoir chamber and vacuum chamber), initially without a fluid connection between the two. The fact that the membrane and the pointed member are axially slidable in relation to each other implies that the pointed member can penetrate and break the membrane when they meet if the pointed member is configured such that the pointed end of the pointed member points towards the membrane. Preferably, in such a design the pointed member is attached inside the barrel, preferably attached at the distal end of the barrel pointing towards the plunger and the membrane. This can be seen as a stable solution compared to having a needle that is moved inside the barrel.

Configurations and Locking Mechanism

The presently disclosed syringe may operate in one or several configurations. In one embodiment the syringe may be configured to retain vacuum in the vacuum chamber in a first configuration, said first configuration preferably being a storage condition of the syringe. In such a configuration the vacuum chamber is a closed container. Such a configuration may be useful not only to store the substance in the vacuum chamber, but can also be considered a "charged" state in that there is in an inherent energy in a vacuum chamber. When a vacuum chamber changes from a closed container to being in connection with another volume, an aspiration force arises. Therefore, if the syringe is configured to retain vacuum in the vacuum chamber in a first configuration, this force could then be released by connecting the vacuum chamber to the reservoir chamber.

In the first configuration, the syringe can be said to be in a state with inherent energy that could later be used to mix the substances of the two chambers, preferably without adding any external manual force to move the plunger.

In the first configuration, the membrane and pointed member are preferably axially separated inside the barrel. This ensures that the vacuum chamber remains a closed volume, retaining the vacuum, until the pointed member penetrates the membrane.

In one embodiment, the syringe is, in a second configuration, configured to provide a liquid communication between the vacuum chamber and the reservoir chamber.

Preferably, in this configuration the pointed member penetrates the membrane. The pointed member can be said to create the liquid communication between the two chambers. If vacuum has been applied to the vacuum chamber in the first configuration, the second configuration may then serve as a configuration in which the two substances are mixed in the vacuum chamber. This is achieved by the aspirating force from the vacuum chamber in combination with that fact that the two chambers now are in liquid communication. According to this description, the reservoir chamber and the vacuum chamber may therefore be fluidly disconnected in a first configuration, and fluidly connected in a second configuration.

The presently disclosure also relates to mechanical means for implementing the abovementioned configurations. In the first configuration, the membrane and pointed member are preferably axially separated inside the barrel while vacuum is retained in the vacuum chamber. As stated, in the vacuum state there is an inherent force that pulls the (typically axially movable) plunger towards the vacuum chamber. The displacement of the plunger can be prevented mechanically by a locking mechanism; therefore, in one embodiment, the presently disclosed syringe further comprises a removable locking member configured to engage and restrict the plunger from distal axial displacement inside the barrel.

There are several ways of implementing such a locking mechanism. In one embodiment, the locking member is configured to engage the proximal part of the plunger extending from the proximal end of the barrel. An example of such a solution is shown in FIG. 1A. In this example, first locking element 9 abuts the plunger flange 11 and prevents the plunger from moving towards the vacuum chamber. In one embodiment, the first position is determined by the first and second locking elements engaging the plunger in combination, and wherein the second position is determined by only the second locking element engaging the plunger. In the mentioned example (FIGS. 1A and 1B), the first locking element is indirectly locked by the upper side of the barrel flange 12 (having a second locking element 10 in between the first locking element 9 and the barrel flange 12). The example shall not be seen as restricting the first locking element to this solution—other mechanical locking solutions of a removable locking member to restrict the plunger from distal axial displacement inside the barrel can be imagined. Therefore, in another embodiment, the locking member is configured to engage and restrict the plunger from distal axial displacement inside the barrel in two different axial positions of the plunger relative to the barrel.

In one embodiment of the presently disclosed syringe, the locking member comprises a first locking element and a second locking element, each of said locking elements configured to engage and restrict the plunger from distal axial displacement inside the barrel. The two locking elements may be placed such that the first and second locking elements are configured to engage the plunger in axial extension of each other. The second locking element can be used to lock the plunger in a second position in relation to the barrel (and possibly the pointed member). In this state the two substances can be mixed in the vacuum chamber, but the plunger is mechanically prevented from being further moved towards the distal end of the barrel to deliver the mixed content. Therefore, in one configuration of the presently disclosed syringe, the axial displacement of the plunger from a first position to a predefined second position penetrates the membrane by the pointed member and establishes a fluid passageway between the reservoir chamber and the vacuum chamber. Examples of the two configurations are shown in FIG. 1A and b respectively. In one embodiment the first configuration corresponds to a first axial position of the plunger (FIG. 1A, first and second locking element present) in the barrel and the second configuration corresponds to a second axial position of the plunger in the barrel (FIG. 1B, first locking element removed, second locking element present). As stated, and as can be seen in the example in FIGS. 1A and 1B, in one embodiment the syringe is configured such that the plunger is locked in a first configuration, and, in one embodiment the syringe is configured such that the plunger is locked in said second configuration.

In one embodiment, the presently disclosed syringe is configured such that the plunger is restricted from axial displacement in a distal direction in said first configuration, preferably by means of the removable first and second locking elements for engaging and locking the plunger in said first configuration. Distal direction in this context has the meaning that the plunger moves towards the distal end of the barrel. As stated this means, in a preferred embodiment, that the plunger is locked in the distal direction such that the pointed member does not penetrate the membrane and the substance cannot be mixed. When the plunger is unlocked (e.g. by removing the locking member), a vacuum in the vacuum chamber causes an axial displacement of the plunger from a first position to a second position. Similarly, in the second configuration, the plunger may be restricted from axial displacement in a distal direction, preferably by means of the removable second locking element adapted for engaging and locking the plunger in said second configuration.

A further aspect of the presently disclosed syringe relates to the pointed member comprising one or more liquid bypass channels configured to provide liquid communication between the reservoir chamber and the vacuum chamber upon penetration of the membrane, which is further explained below. In relation to the configuration and/or position of the parts of the syringe, the presently disclosed invention presents a solution of how to provide a liquid path between the two chambers upon penetration of the membrane by the pointed member. The inventors have realized that by locking the membrane (preferably located at the distal end of the plunger) in an axial direction in relation to the pointed member, the bypass channel can be positioned such that it allows substance to flow from the reservoir chamber to the vacuum chamber. Therefore, in one embodiment, the syringe is configured such that in the second configuration and/or second position the at least one of said one or more bypass channels are axially aligned with the membrane. An example of such an alignment can be seen in FIG. 1B, in which the bypass channel 15 (small recess or groove in the pointed member) is axially aligned with the membrane 7, such that substance can flow from the reservoir chamber 6 to the vacuum chamber 4.

Membrane and Pointed Member

As stated, the presently disclosed syringe has a membrane separating the vacuum chamber and the reservoir chamber, and a pointed member, such as one or more needles, for penetrating the membrane. In a preferred embodiment, the membrane separates a proximal end of the vacuum chamber and a distal end of the reservoir chamber. In one embodiment, the membrane is attached to and/or forms the distal end of the plunger. If the plunger has a hollow body or hollow portion, this means that the membrane constitutes a portion or the whole of the bottom/distal side of the plunger. An example of such an implementation is shown in FIGS. 1A-F. A plunger of a syringe may be cylindrical having a rounded end (like a test tube) or a substantially flat distal end, wherein the distal end is substantially circular in the case of a cylindrical shape of the plunger. Therefore, in one embodiment, a part of the distal end may be replaced by a material that can be penetrated by the pointed member. Preferably, the plunger is made of a hard material, such as plastic, and the membrane is made of a soft/softer material, e.g. rubber like material. The idea of this embodiment is that the pointed member should penetrate the membrane upon a distal displacement of the plunger inside the barrel. In this regard the plunger (including the membrane) can be considered to be the moving part of the design, whereas the barrel can be considered to be the fixed part. The syringe preferably comprises a sealed engagement between the plunger and barrel, e.g. in the form of a rubber seal in a distal end of the plunger, also helping to retain a vacuum in the vacuum chamber in the first configuration of the presently disclosed syringe. As illustrated in FIG. 3 the membrane 7 can be attached to the distal end of the plunger 5 via annular protrusion 19. The membrane 7 comprises the penetratable membrane barrier 7' and a sealing flange 20 providing a sealed engagement with the barrel 2.

In one embodiment the pointed member is attached inside the barrel, preferably attached at the distal end of the barrel. In this configuration, the pointed member and the membrane can move in relation to each other. The pointed member preferably extends axially inside the barrel, i.e. in the longitudinal direction of the barrel. In the example in FIG. 1A it can be seen how the pointed member is attached to the distal end of the barrel, extending axially inside the barrel from the distal end of the barrel and pointing towards the proximal end of the barrel.

Figure 1B:
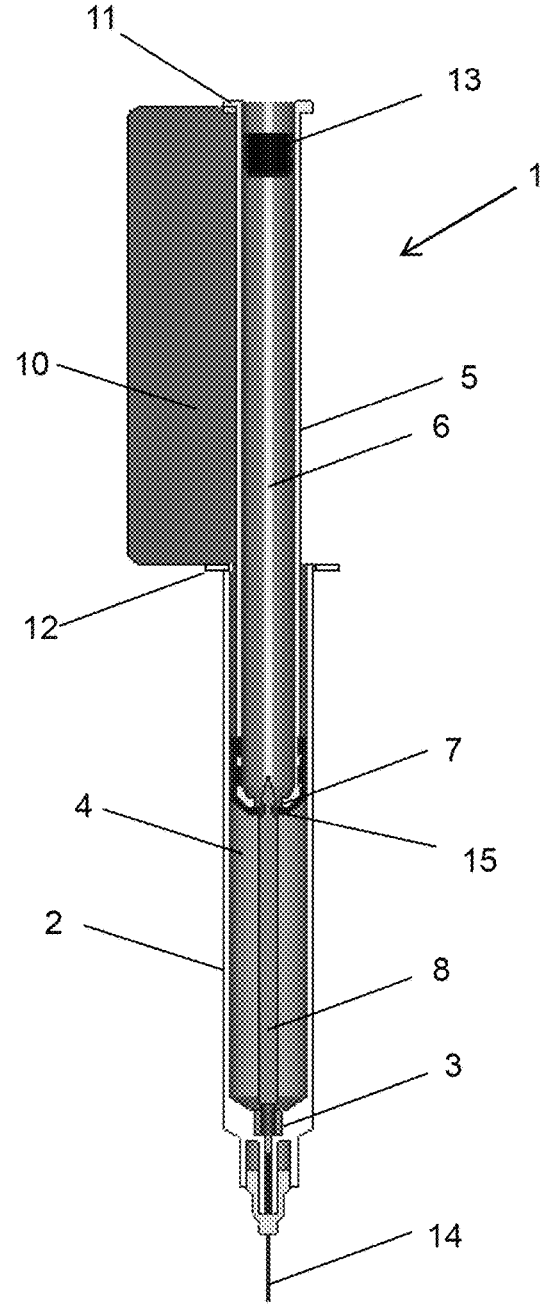
FIG. 1B shows the syringe of FIG. 1A where the first locking element has been removed and the aspiration force by the vacuum in the vacuum chamber has moved the plunger to a position in which a second substance in the reservoir chamber is transferred to the vacuum chamber through an axial separation section between the pointed member and the membrane. A second locking element prevents the plunger form moving further towards the vacuum chamber.
Figure 1C:
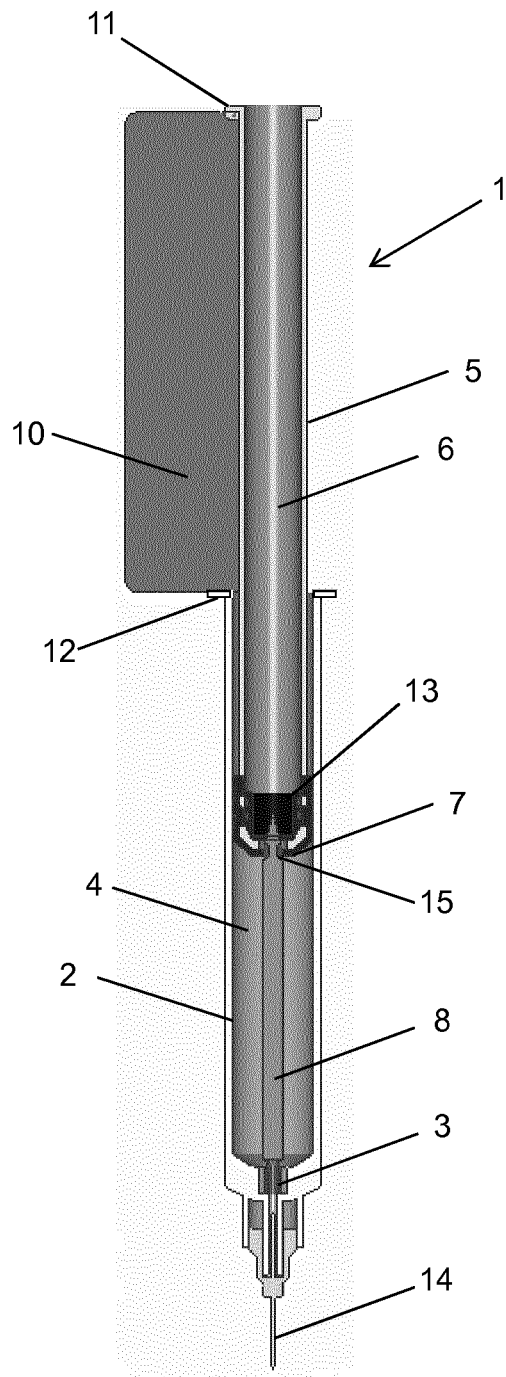
FIG. 1C shows the syringe of FIG. 1A-B where the vacuum in the vacuum chamber has emptied the reservoir chamber and moved the plug to abut the membrane. The second locking element still prevents the plunger from moving further towards the vacuum chamber.

As stated, the idea of having a pointed member that can penetrate the membrane between the reservoir chamber and the vacuum chamber is to provide a bypass channel that makes use of the vacuum of the vacuum chamber to aspirate substance from the reservoir chamber to mix with the substance of the vacuum chamber. Therefore, in one embodiment of the presently disclosed syringe, the pointed member comprises one or more liquid bypass channels configured to provide liquid communication between the reservoir chamber and the vacuum chamber upon penetration of the membrane. The liquid bypass channel could be in the form of a hollow needle. The liquid bypass channel could also make use of the locking mechanism and second configuration described above. The inventors have realized that if the second configuration corresponds to a second locked axial position of the plunger in the barrel, this known position can be used to design the liquid bypass channel. As can be seen in e.g. FIG. 1B, a locking mechanism ensures that the pointed member and the member have a predefined locked position in relation to each other. In this configuration the liquid communication between the reservoir chamber and the vacuum chamber is provided for predefined axial position of the plunger, preferably only for said predefined axial position. In FIG. 1B the bypass channel 15 is axially aligned with the membrane, thereby providing a liquid path between the reservoir chamber and the vacuum chamber through small recesses of the pointed member. Since the pointed member is radially thinner in level with the recesses, and a radically thicker part has penetrated the membrane to reach this locked position, the membrane can be considered to have an opening that is larger than the cross-section of the pointed member in level with the recesses, thereby providing a liquid bypass channel between the two chambers. A further advantage of the liquid bypass channel formed as a recess as exemplified in the drawings is that the liquid (and fluid) communication is only established in one predefined axial position of the plunger relative to the barrel. If the plunger is moved further distally inside the plunger, as illustrated in FIGS. 1E and 1F, the liquid (and fluid) communication between the reservoir chamber and the vacuum chamber is closed again if the membrane and the pointed member are configured to provide a fluid and/or liquid tight engagement when the membrane is penetrated by the pointed member but the membrane is separated from the liquid bypass channel. Hence, the presently disclosed syringe may be configured such that the membrane and the pointed member form a sealed engagement when the pointed member penetrates the membrane and the membrane is axially separated from said one or more liquid bypass channels.

"Pointed" in relation to the presently disclosed syringe should be construed broadly in the sense that it could be any pointed structure capable of penetrating or breaking the membrane, typically a structure having a sharp top, such as a needle. In one embodiment, the pointed member is formed as an elongated pointed element wherein one end of the pointed element, preferably the proximal end, is pointed, such as pointed like a needle. Proximal is defined in the same way as proximal of the plunger and the barrel, i.e. opposite to distal i.e. opposite to the outlet and outer needle of the syringe.

In one embodiment, the liquid bypass channels are located adjacent to the proximal end of the pointed member. This has the advantage that the rest of the pointed member (i.e. below the bypass channel towards the distal part of the vacuum chamber) can be maintained as a mixing container in the locked second position. In one embodiment, one or more liquid bypass channels are formed as one or more recesses, such as one or more radial recesses, of the pointed member located distal from the proximal part of the pointed element. The liquid bypass channels, formed as one or more recesses, may be placed less than 1 mm, or less than 2 mm, or less than 3 mm, or less than 4 mm, or less than 5 mm, or less than 6 mm, or less than 7 mm, or less than 8 mm, or less than 10 mm, or less than 12 mm, or less than 14 mm, or less than 16 mm, or less than 18 mm, or less than 20 mm from the proximal end of the pointed member.

Plug

In a further embodiment of the presently disclosed invention, the syringe further comprises an axially slidable plug inside the plunger, preferably sealably engaged with the inside of the plunger which may be hollow, such that the reservoir chamber can be defined (proximally) by the plug inside the hollow plunger. This means that the plug can constitute a proximate sidewall of the closed reservoir chamber—the reservoir chamber is preferably located in the distal end of the plunger and defined distally by the distal end of the plunger and proximally by the axially slidable plug. Preferably, the plug is axially slidable inside the plunger, and can be used to plug the fluid connection between the two chambers when the substance of the reservoir of the first chamber has been transferred to the vacuum chamber. Since the plug defines a proximate sidewall of the reservoir, the reservoir chamber can alternatively be seen as an empty or nearly empty volume when the plug has been aspirated to a distal position abutting the distal end of the plunger or the member. In this position the content of the reservoir chamber has been transferred to the vacuum chamber.

Since, in one embodiment, the pointed member protrudes through the membrane after having penetrated the membrane, in a preferred embodiment the plug is made of a material that can also be penetrated by the pointed member, which allows that the plug is aspirated by the vacuum of the vacuum chamber to a position in which it abuts the distal end of the plunger or the member.

In a preferred embodiment, the plug is placed inside the plunger, and in an even more preferred embodiment, the plug is completely contained within the hollow body of the plunger. If the plunger is cylindrical, i.e. having a substantially circular cross-section, the plug should also have a substantially similar cross-section in order to seal the reservoir chamber. In this kind of embodiment, the plug can be considered to be recessed within the hollow body of the plunger. Preferably, the axially slidable plug is suitable for being penetrated by the pointed member, preferably only by means of the aspiration force exerted by the vacuum in the vacuum chamber.

When the discharge/transfer of substance from the reservoir chamber to the vacuum chamber takes place, the plug is typically aspirated towards the distal end of the plunger. Therefore, in one configuration of the presently disclosed syringe, upon penetration of the membrane and provision of a liquid communication between the vacuum chamber and the reservoir chamber, a vacuum in the vacuum chamber draws liquid contained in the reservoir chamber into the vacuum chamber along with an axial distal displacement of the plug within the hollow body. Furthermore, in such a configuration, the plug is configured to be axially displaced distally within the hollow body of the plunger during discharge/flushing of the second substance in the reservoir chamber into the vacuum chamber.

Other embodiments of the plug are also possible. The plug can be made of an expandable or elastic material, or, alternatively, the plug can be formed as a second small plunger adapted to fit and be recessed within the hollow plunger. Besides the advantage that plungers have proved to work for the purpose of keeping an inner volume sealed and push the volume to deliver it through a needle or other liquid connection, it opens the possibility for having a third chamber (i.e. a second separate reservoir) in the second plunger and mix more than two substances.

Vacuum Bypass Channel

Figure 2:
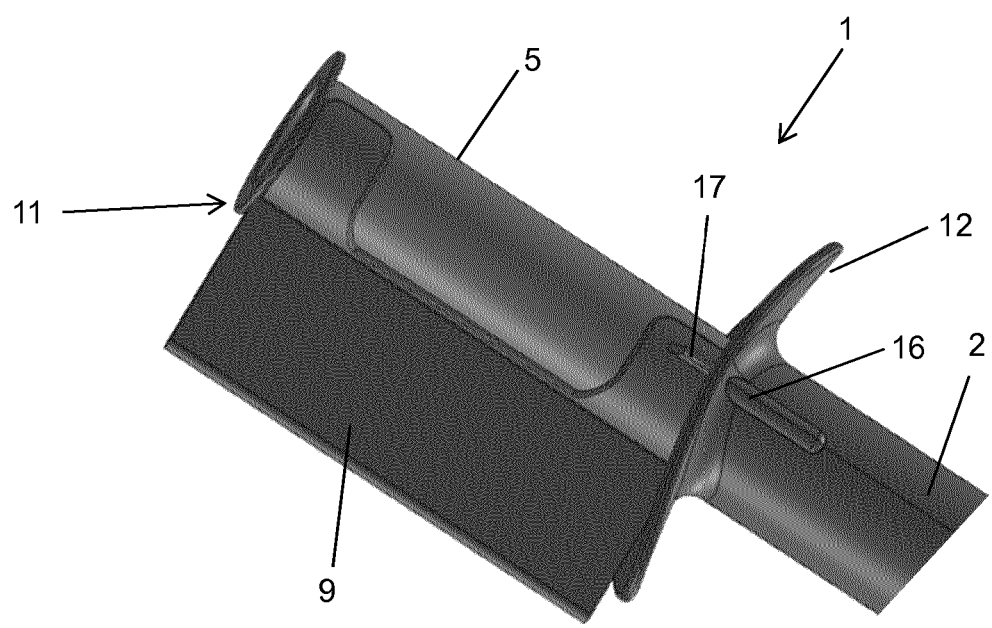
FIG. 2 shows the proximal end of one embodiment of the presently disclosed syringe with a locking element engaging the plunger, a vacuum bypass channels, and a longitudinal protrusions adapted to match the vacuum bypass channel.

As stated, the presently disclosed invention relates to a syringe including a vacuum chamber for holding a first substance. There are several ways of achieving vacuum in a closed volume (chamber). One embodiment of the presently disclosed syringe further comprising one or more vacuum bypass channels located in the barrel and/or in the plunger and configured such that the plunger sealably engages the vacuum chamber in at least a first axial position of the plunger inside the vacuum chamber, i.e. the state where a vacuum is retained, and such that fluid communication is established across the plunger in at least a second axial position of the plunger inside the vacuum chamber via said one or more vacuum bypass channels. Thus, the vacuum bypass channel(s) may be configured to break the sealing between the vacuum chamber and the plunger at a predefined axial position of the plunger inside the vacuum chamber. This may for example be provided if said one or more vacuum bypass channels 16 are one or more longitudinal grooves 17 formed in the inner surface of the proximal end of the vacuum chamber as illustrated in FIG. 2. Alternatively the one or more vacuum bypass channels may be formed in the plunger. One or more vacuum bypass channels are configured such that a fluid communication can be provided directly between the vacuum chamber and the ambient atmosphere independent of the position of the plunger, e.g. via a pressure valve located directly at the vacuum chamber.

Substances

The presently disclosed syringe works for a number of different substances in the two chambers. Some types of medication are provided and stored in two separate chambers, and are mixed before use. Such medication may include a solid component and a liquid solvent and are known as two-part formulations. The solid component can be for example a powdered medicament. In one embodiment of the syringe, the chambers are prefilled with first and second substances, wherein the first substance is a dry composition, and wherein the second substance is an aqueous medium. Preferably, the dry composition is placed in the vacuum chamber and the aqueous medium in the reservoir chamber. Similarly, the syringe may be prefilled with first and second substances, wherein the first substance is a dry component of a medicament and wherein the second substance is an aqueous medium in a wet component of said medicament. The presently disclosed syringe is also suitable for being used with a lyophilized substance, such as a lyophilized drug, as the first substance.

Other Barrel and Plunger Related Aspects

The barrel preferably comprises an outlet for disposing the mixed final product. This outlet is preferably closable and/or sealable in order to retain the vacuum in the vacuum chamber. The outlet may e.g. be a Luer type outlet and it is advantageously located at the distal end of the barrel. The outlet may further be formed as a connector portion suitable for connecting with another mating connector, e.g. suitable for connecting a hose to the syringe. The connector portion may be a connector portion of a standard type, such as a Luer lock or Luer slip connector, preferably a male Luer lock or Luer slip connector. The connector portion may be provided with a threaded portion for secure connection with matching connector. This threaded portion may be provided at the inside of the connector portion.

Preferably, the barrel has an open proximal end, wherein the plunger extends through the proximal end, which can be considered to be a standard solution for a syringe. Typically the syringe is configured such that the plunger can be axially displaced through an open proximal end of the barrel.

The volume capacity presently disclosed syringe is scalable by shaping and scaling the barrel and the plunger. The volume of the vacuum chamber and the reservoir chamber can then be selected within the limits of the barrel and the plunger. The volume of the barrel and/or the volume of the vacuum chamber may be between 0.1 and 500 mL, more preferred between 1 and 100 mL, more preferred between 2 and 50 mL, more preferred between 3 and 30 mL, more preferred less than 25 mL, more preferred less than 20 mL, more preferred less than 15 mL, more preferred less than 10 mL, most preferred between 5 and 10 mL.

Correspondingly the volume of the hollow body of the plunger and/or the volume of the reservoir chamber is between 0.1 and 500 mL, more preferred between 1 and 100 mL, more preferred between 2 and 50 mL, more preferred between 3 and 30 mL, more preferred less than 25 mL, more preferred less than 20 mL, more preferred less than 15 mL, more preferred less than 10 mL, most preferred between 5 and 10 mL.

The presently disclosed syringe is preferably a single-use disposable syringe. The different components of the syringe (barrel, plunger, plug, valve, valve part, etc.) are preferably suitable for manufacture by means of single cycle injection molding.

Examples

One embodiment of the presently disclosed syringe 1 is exemplified in FIGS. 1A-1F. The barrel 2 is provided with a vacuum chamber 4, an outlet 3, an outer needle 14 and a barrel flange 12. The plunger 5 has a reservoir chamber 6 and a plunger flange 11. The membrane 7 forms the distal end of the plunger 5. Inside the barrel 2 there is a pointed member 8 attached at the distal end of the barrel 2, the pointed member 8 having a bypass channel 15. The syringe further comprises an (axially slidable) plug 13 inside the plunger 5, sealably engaged with the inside of the plunger 5. The syringe also comprises first and second locking elements 9 and 10, respectively, to lock the positions of the plunger 5 and barrel 2) in relation to each other (i.e. also the positions between the membrane and the pointed member in relation to each other).

FIGS. 1A-F can be said to show a process in which the syringe goes from a preloaded state having two substances separated in the vacuum chamber 4 and the reservoir chamber 6, through a state where the substances are mixed, and finally the mixed substance delivered.

In FIG. 1A the syringe 1 is locked in a first configuration. In this configuration a vacuum generator can be connected to the vacuum chamber 4 and vacuum created, thereby building up inherent energy of the syringe and a vacuum force pulling the plunger 5 towards the vacuum chamber 4. However, the first and second locking element 9 and 10 prevent the plunger from moving.

In FIG. 1B the first locking element 9 has been removed and, as a consequence, the plunger has been pulled by the vacuum force to a second position, where it is blocked from further moving by the second locking element 10. The pointed member 8 has penetrated the membrane 7 and the first substance can start to flow from the reservoir chamber 6 to the vacuum chamber 4 through the bypass channel 15, which is axially aligned with the (penetrated) membrane 7.

In FIG. 10 the content (substance) of the reservoir chamber 6 has been transferred to the vacuum chamber 4, where the two substances have been mixed. The plug 13 has also been pulled by the vacuum force to abut the distal end of the plunger 5.

Figure 1D:
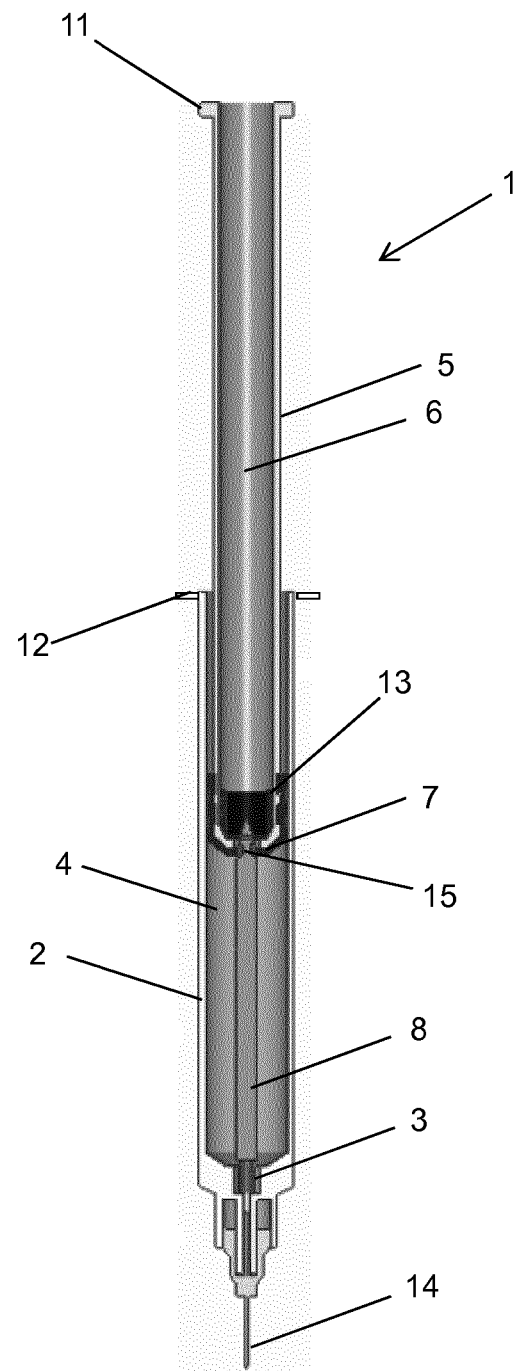
FIG. 1D shows the syringe of FIG. 1A-C where the second locking element has been removed. The plug abuts the membrane. In this configuration the plunger can be pushed downwards to deliver the mixed content in the vacuum chamber through the outlet of the syringe.
Figure 1E:
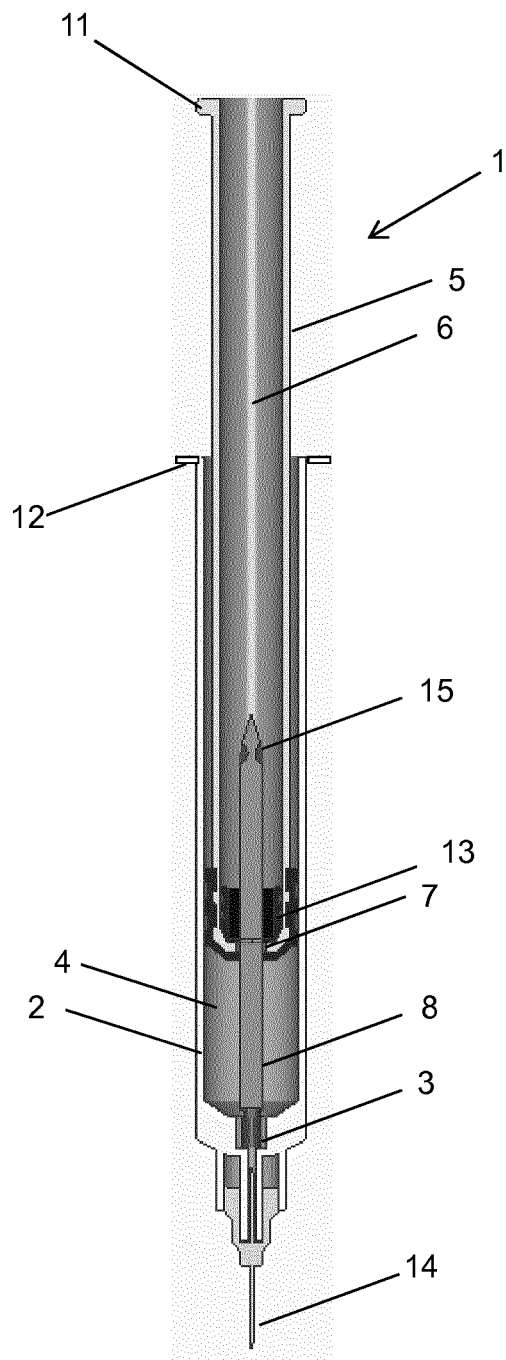
FIG. 1E shows the syringe of FIG. 1A-D where the plunger and plug has been pushed downwards towards the vacuum chamber to empty the content of the vacuum chamber. The plug has been penetrated by the pointed member in this position.
Figure 1F:
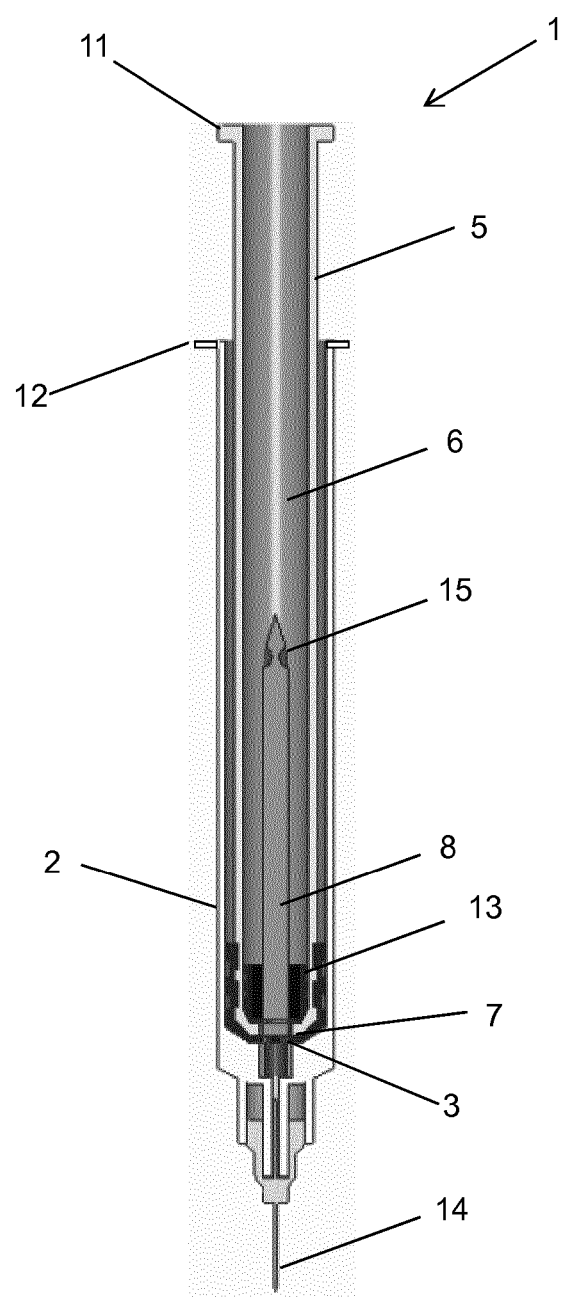
FIG. 1F shows the syringe of FIG. 1A-E in the position where all the content of the vacuum chamber has been emptied by pushing the plunger to a final position.

In FIG. 1D the second locking element 10 has been removed, enabling the possibility to push the plunger 5 further towards the vacuum chamber 4 to eject the mixed content through the outlet 3 and outer needle 14.

In FIG. 1E the plunger 5 has been pushed (or further pulled by the vacuum force) further towards the vacuum chamber 4. Finally, in FIG. 1F the mixed content has been ejected/delivered by pushing plunger 5 in the distal direction to a final position.

FIG. 2 shows the proximal part of the syringe 1 where a first locking element 9 is snap fitted to the proximal end of the plunger 5 restricting that the plunger 5 can be moved in a distal direction into the barrel 2. The barrel 2 comprises vacuum bypass channel 16. The first locking element 9 is provided with longitudinal protrusion 17 adapted to match the vacuum bypass channel 16 in the barrel 2. The first locking element 9 is a rigid plastic element that grabs the proximal part of the plunger 5 and the rigidity and the extension of the locking element 9 locks the plunger 5 in an axial position relative to the barrel 2 defined by the length of the locking element 9. The locking element 9 does not prevent the plunger 5 from moving in a proximal direction out of the barrel 2. However, when a vacuum is retained in the vacuum chamber, the lower pressure of the vacuum will draw the plunger 5 towards the vacuum chamber. I.e. the syringe is configured such that the plunger 5 can be locked in the barrel 2, i.e. restricted from longitudinal/axial movement in both the proximal and distal direction. The longitudinal protrusion 17 in the locking element 9 is adapted to match the vacuum bypass channels 16 in the barrel 2 to provide a rotational lock of the locking element 9 in this locked configuration helping to ensure that the syringe 1 cannot be easily tampered with in the locked configuration.

FIGS. 3A and 3B show illustrations of an exemplary plunger 5 of the presently disclosed syringe. The plunger 5 comprises a plunger flange 11 and a reservoir chamber 6 which is defined by the slidable plug 13 (not shown in FIG. 3). The membrane 7 is attached to the distal end of the plunger 5. The membrane 7 comprises an annular protrusion 20 such that the plunger engages sealingly with the inside of the barrel 2. The membrane 7 further comprises a thin membrane barrier 7' that can be penetrated by the pointed member 8. The membrane is attached to the plunger by engagement with the circular protrusion 19. The plunger further comprises longitudinal protrusions 18 adapted to match the vacuum bypass channels 16 in the barrel 2 and/or the longitudinal protrusions 17 of the first locking element 9.

Further Details of the Invention

1. A syringe for retaining and mixing first and second substances comprising
   a barrel comprising a sealable and/or closable distal outlet and a vacuum chamber for holding a first substance,
   a plunger incorporating a reservoir chamber for holding a second substance and configured to be axially displaced through a proximal end of the barrel,
   a membrane separating the vacuum chamber and the reservoir chamber, and
   a pointed member, such as one or more needles, for penetrating the membrane,
   wherein the syringe is configured such that the membrane and the pointed member are axially slidable in relation to each other.
2. The syringe according to any of the preceding items, wherein the reservoir chamber is (completely) contained in the plunger, and/or wherein the reservoir chamber is at least partly defined by outer walls of the plunger.
3. The syringe according to any of the preceding items, wherein an axial displacement of the plunger relative to the barrel corresponds to an axial displacement of the membrane and the pointed member relative to each other.
4. The syringe according to any of the preceding items, wherein the syringe is configured such that the membrane and the pointed member are axially slidable in relation to each other in correspondence with an axial displacement of the barrel relative to the plunger.
5. The syringe according to any of the preceding items, configured such that an axial displacement of the plunger from a first position to a predefined second position in the barrel penetrates the membrane by the pointed member and establishes a fluid passageway between the reservoir chamber and the vacuum chamber.
6. The syringe according to any of the preceding items 5, whereupon the vacuum in the vacuum chamber aspirates the second substance into the vacuum chamber thereby transferring the content of the reservoir chamber into the vacuum chamber, preferably without displacement of the plunger from said predefined second position.
7. The syringe according to any of the preceding items, configured to retain a vacuum in the vacuum chamber in a first configuration, said first configuration preferably being a storage condition of the syringe.
8. The syringe according to item 7, configured such that in said first configuration the membrane and the pointed member are separated, preferably axially separated inside the barrel.
9. The syringe according to any of the preceding items, configured to provide a liquid communication between the vacuum chamber and the reservoir chamber in a second configuration.
10. The syringe according to item 9, configured such that in said second configuration the pointed member penetrates the membrane.
11. The syringe according to any of the preceding items 9-10, further comprising a liquid bypass arrangement and configured such that said liquid communication between the vacuum chamber and the reservoir chamber is provided by means of said liquid bypass arrangement.
12. The syringe according to any of the preceding items, wherein the membrane is separating a proximal end of the vacuum chamber and a distal end of the reservoir chamber.
13. The syringe according to any of the preceding items, configured such that the pointed member penetrates the membrane upon a distal displacement of the plunger inside the barrel.
14. The syringe according to any of the preceding items, wherein the membrane is attached to and/or forms the distal end of the plunger.
15. The syringe according to any of the preceding items, wherein the pointed member is attached inside the barrel, preferably attached at the distal end of the barrel.
16. The syringe according to any of the preceding items, wherein the pointed member is extending axially inside the barrel.
17. The syringe according to any of the preceding items, wherein the pointed member is extending axially inside the barrel from the distal end of the barrel and pointing towards the proximal end of the barrel.
18. The syringe according to any of the preceding items, wherein the pointed member comprises one or more liquid bypass channels configured to provide liquid communication between the reservoir chamber and the vacuum chamber upon penetration of the membrane.
19. The syringe according to item 18, wherein said liquid communication between the reservoir chamber and the vacuum chamber is provided for predefined axial position of the plunger, preferably only for said predefined axial position.
20. The syringe according to any of the preceding items 18-19, configured such that the membrane and the pointed member form a sealed engagement when the pointed member penetrates the membrane and the membrane is axially separated from said one or more liquid bypass channels.
21. The syringe according to any of the preceding items, further comprising a removable locking member configured to engage and restrict the plunger from distal axial displacement inside the barrel.
22. The syringe according to item 21, wherein the locking member is configured to engage the proximal part of the plunger extending from the proximal end of the barrel.
23. The syringe according to any of the preceding items 21-22, wherein the locking member is configured to engage and restrict the plunger from distal axial displacement inside the barrel in two different axial positions of the plunger relative to the barrel.
24. The syringe according to any of the preceding items 21-23, wherein the locking member comprises a first locking element and a second locking element, each of said locking elements configured to engage and restrict the plunger from distal axial displacement inside the barrel.
25. The syringe according to item 24, wherein the first and second locking elements are configured to engage the plunger in axial extension of each other.
26. The syringe according to any of the preceding items, wherein the first configuration corresponds to a first axial position of the plunger in the barrel and wherein the second configuration corresponds to a second axial position of the plunger in the barrel.

27. The syringe according to any of the preceding items, configured such that the plunger is locked in said first configuration.
28. The syringe according to any of the preceding items, configured such that the plunger is locked in said second configuration.
29. The syringe according to any of the preceding items, configured such that the plunger is restricted from axial displacement in a distal direction in said first configuration, preferably by means of the removable first and second locking elements for engaging and locking the plunger in said first configuration.
30. The syringe according to any of the preceding items, configured such that the plunger is restricted from axial displacement in a distal direction in said second configuration, preferably by means of the removable second locking element adapted for engaging and locking the plunger in said second configuration.
31. The syringe according to any of the preceding items, configured such that upon unlocking the plunger, a vacuum in the vacuum chamber causes an axial displacement of the plunger from a first position to a second position.
32. The syringe according to any of the preceding items, configured such that an axial displacement of the plunger from a first position to a predefined second position penetrates the membrane by the pointed member and establishes a fluid passageway between the reservoir chamber and the vacuum chamber.
33. The syringe according to item 32, wherein the first position is determined by the first and second locking elements engaging the plunger in combination, and wherein the second position is determined by only the second locking element engaging the plunger.
34. The syringe according to any of the preceding items, wherein the plunger is hollow.
35. The syringe according to any of the preceding items, further comprising an axially slidable plug inside the plunger, said plug sealably engaged with the inside of the plunger which is hollow, such that the reservoir chamber is defined by the plug inside the hollow plunger.
36. The syringe according to item 35, wherein the reservoir chamber is located in the distal end of the plunger and defined distally by the distal end of the plunger and proximally by the axially slidable plug.
37. The syringe according to any of the preceding items 35-36, wherein the plug is completely contained within the hollow body of the plunger
38. The syringe according to any of the preceding items 35-37, wherein the plug is recessed within the hollow body of the plunger,
39. The syringe according to any of the preceding items 35-38, wherein the plug is configured to be axially displaced distally within the hollow body of the plunger during discharge/flushing of the second substance in the reservoir chamber into the vacuum chamber.
40. The syringe according to any of the preceding items 35-39, configured such that upon penetration of the membrane and provision of a liquid communication between the vacuum chamber and the reservoir chamber, a vacuum in the vacuum chamber draws liquid contained in the reservoir chamber into the vacuum chamber along with an axial distal displacement of the plug within the hollow body.
41. The syringe according to any of the preceding items 35-40, wherein the axially slidable plug is configured to be penetrated by the pointed member.
42. The syringe according to any of the preceding items, wherein the pointed member is formed as an elongated pointed element wherein one end of the pointed element, preferably the proximal end, is pointed, such as pointed like a needle.
43. The syringe according to any of the preceding items, wherein the pointed member comprises one or more liquid bypass channels.
44. The syringe according to item 43, wherein said one or more liquid bypass channels are located adjacent to the proximal end of the pointed member.
45. The syringe according to any of the preceding items 43-44, wherein said one or more liquid bypass channels are formed as one or more recesses, such as one or more radial recesses, of the pointed member located distal from the proximal part of the pointed element.
46. The syringe according to any of the preceding items 43-45, configured such that in said second configuration and/or second position the at least one of said one or more bypass channels are axially aligned with the membrane.
47. The syringe according to any of the preceding items, further comprising one or more vacuum bypass channels located in the barrel and/or in the plunger and configured such that the plunger sealably engages the vacuum chamber in at least a first axial position of the plunger inside the vacuum chamber, and such that fluid communication is established across the plunger in at least a second axial position of the plunger inside the vacuum chamber via said one or more vacuum bypass channels.
48. The syringe according to any of the preceding items, wherein the syringe is prefilled with first and second substances and wherein the first substance is a dry composition, and wherein the second substance is an aqueous medium.
49. The syringe according to any of the preceding items, wherein the syringe is prefilled with first and second substances and wherein the first substance is a dry component of a medicament and wherein the second substance is an aqueous medium in a wet component of said medicament.
50. The syringe according to any of the preceding items, wherein the first substance is a lyophilized substance, such as a lyophilized drug.
51. The syringe according to any of the preceding items, wherein the barrel comprises an open proximal end.
52. The syringe according to any of the preceding items, configured such that a proximal end of the plunger extends through an open proximal end of the barrel.
53. The syringe according to any of the preceding items, configured such that the plunger can be axially displaced through an open proximal end of the barrel.
54. The syringe according to any of the preceding items, wherein the barrel comprises a sealable/closable outlet, such as a Luer type outlet.
55. The syringe according to any of the preceding items, wherein the barrel comprises a sealable/closable outlet located at the distal end of the barrel.
56. The syringe according to any of the preceding items, wherein the outlet comprises a connector portion at a distal end, such as a Luer type connector portion.

57. The syringe according to any of the preceding items, further comprising a sealed engagement between the plunger and barrel.
58. The syringe according to any of the preceding items, wherein the reservoir chamber is defined by a hollow portion of the plunger.
59. The syringe according to any of the preceding items, wherein the plug is formed as a small plunger adapted to fit and be recessed within the hollow plunger.
60. The syringe according to any of the preceding items, wherein the reservoir chamber and the vacuum chamber are fluidly disconnected in said first configuration.
61. The syringe according to any of the preceding items, wherein the reservoir chamber and the vacuum chamber are fluidly connected in said second configuration.
62. The syringe according to any of preceding items, wherein said one or more vacuum bypass channels are configured to break the sealing between the vacuum chamber and the plunger at a predefined axial position of the plunger inside the vacuum chamber.
63. The syringe according to any of preceding items, wherein said one or more vacuum bypass channels are one or more longitudinal grooves formed in the inner surface of the proximal end of the vacuum chamber.
64. The syringe according to any of preceding items, wherein said one or more vacuum bypass channels are formed in the plunger.
65. The syringe according to any of preceding items, wherein the volume of the barrel and/or the volume of the vacuum chamber is between 0.1 and 500 mL, more preferred between 1 and 100 mL, more preferred between 2 and 50 mL, more preferred between 3 and 30 mL, more preferred less than 25 mL, more preferred less than 20 mL, more preferred less than 15 mL, more preferred less than 10 mL, most preferred between 5 and 10 mL.
66. The syringe according to any of preceding items, wherein the volume of the hollow body of the plunger and/or the volume of the reservoir chamber is between 0.1 and 500 mL, more preferred between 1 and 100 mL, more preferred between 2 and 50 mL, more preferred between 3 and 30 mL, more preferred less than 25 mL, more preferred less than 20 mL, more preferred less than 15 mL, more preferred less than 10 mL, most preferred between 5 and 10 mL.
67. The syringe according to any of preceding items, wherein the barrel, the plunger, the plug, the valve and/or the axially displaceable valve element is/are suitable for manufacture by means of single cycle injection moulding.

The invention claimed is:

1. A syringe for retaining and mixing first and second substances comprising:
   a barrel comprising a sealable and/or closable distal outlet and a vacuum chamber for retaining the first substance in a vacuum,
   a plunger incorporating a reservoir chamber for holding the second substance and configured to be axially displaced through a proximal end of the barrel,
   a membrane separating the vacuum chamber and the reservoir chamber, and
   a pointed member for penetrating the membrane,
   wherein the syringe is configured such that the vacuum in the vacuum chamber pulls the plunger without involvement of a manual force on the plunger to effectuate an axial displacement of the plunger from a first position in which the pointed member does not penetrate the membrane to a predefined second position in the barrel and this axial displacement of the plunger penetrates the membrane by the pointed member and establishes a fluid passageway between the reservoir chamber and the vacuum chamber whereupon the vacuum in the vacuum chamber aspirates the second substance into the vacuum chamber thereby transferring the second substance of the reservoir chamber into the vacuum chamber without displacement of the plunger from said predefined second position.

2. The syringe according to claim 1, configured to retain the vacuum in the vacuum chamber in a first configuration.

3. The syringe according to claim 2, wherein the first configuration corresponds to the first position of the plunger in the barrel and wherein a second configuration corresponds to the predefined second position of the plunger in the barrel.

4. The syringe according to claim 3, configured such that the plunger is locked in said second configuration.

5. The syringe according to claim 2, configured such that the plunger is locked in said first configuration.

6. The syringe according to claim 2, wherein said first configuration is a storage condition of the syringe.

7. The syringe according to claim 1, wherein the pointed member is attached inside the barrel.

8. The syringe according to claim 1, wherein the pointed member is attached at a distal end of the barrel.

9. The syringe according to claim 1, further comprising a removable locking member configured to engage and restrict the plunger from distal axial displacement inside the barrel, said locking member comprising a first locking element and a second locking element, each of said locking elements configured to engage and restrict the plunger from the distal axial displacement inside the barrel.

10. The syringe according to claim 9, wherein the removable locking member is configured to engage and restrict the plunger from the distal axial displacement inside the barrel in two different axial positions of the plunger relative to the barrel: the first position and the predefined second position.

11. The syringe according to claim 10, wherein the two different axial positions of the plunger relative to the barrel correspond to said first position and said predefined second position of the plunger in the barrel, respectively.

12. The syringe according to claim 9, wherein the first and second locking elements are configured to engage the plunger in axial extension of each other.

13. The syringe according to claim 9, configured such that the plunger is restricted from axial displacement in a distal direction in said first configuration by means of the removable first and second locking elements for engaging and locking the plunger in a first configuration.

14. The syringe according to claim 9, configured such that the plunger is restricted from the axial displacement in a distal direction in a second configuration by means of the second locking element adapted for engaging and locking the plunger in the second configuration.

15. The syringe according to claim 1, further comprising an axially slidable plug inside the plunger, said plug being sealably engaged with the inside of the plunger which is hollow, such that the reservoir chamber is defined by the plug inside the hollow plunger.

16. The syringe according to claim 15, wherein the plug is configured to be axially displaced distally within a hollow body of the plunger during discharge/flushing/transfer of the second substance in the reservoir chamber into the vacuum chamber.

17. The syringe according to claim 15, configured such that upon penetration of the membrane and provision of a liquid communication between the vacuum chamber and the reservoir chamber, the vacuum in the vacuum chamber draws the second substance contained in the reservoir chamber into the vacuum chamber along with an axial distal displacement of the plug within the hollow body.

18. The syringe according to claim 1, wherein the pointed member comprises one or more liquid bypass channels configured to provide liquid communication between the reservoir chamber and the vacuum chamber upon penetration of the membrane.

19. The syringe according to claim 18, configured such that the membrane and the pointed member form a sealed engagement when the pointed member penetrates the membrane and the membrane is axially separated from said one or more liquid bypass channels.

20. The syringe according to claim 1, wherein the pointed member comprises one or more liquid bypass channels, said one or more liquid bypass channels formed as at least one recess of the pointed member located distal from a proximal part of the pointed member.

21. The syringe according to claim 20, configured such that in a second configuration and/or the predefined second position the at least one of said one or more bypass channels are axially aligned with the membrane.

22. The syringe according to claim 20, wherein said at least one recess is a radial recess.

23. The syringe according to claim 1, wherein the reservoir chamber is defined by a hollow portion of the plunger and wherein the membrane is attached to and/or forms a distal end of the plunger such that the membrane is separating a proximal end of the vacuum chamber and a distal end of the reservoir chamber.

24. The syringe according to claim 1, wherein the syringe is prefilled with the first and second substances and wherein the first substance is a dry component of a medicament and wherein the second substance is an aqueous medium in a wet component of said medicament.

25. The syringe according to claim 1, wherein the pointed member comprises at least one needle.

* * * * *